(12) United States Patent
Imhof et al.

(10) Patent No.: US 8,663,637 B2
(45) Date of Patent: Mar. 4, 2014

(54) METHODS AND COMPOSITIONS FOR MODULATION OF OLFML3 MEDIATED ANGIOGENESIS

(75) Inventors: Beat A. Imhof, Geneva (CH); Marijana Miljkovic-Licina, Geneva (CH); Philippe Hammel, Geneva (CH)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 13/557,660

(22) Filed: Jul. 25, 2012

(65) Prior Publication Data
US 2013/0034493 A1 Feb. 7, 2013

Related U.S. Application Data

(60) Provisional application No. 61/515,669, filed on Aug. 5, 2011, provisional application No. 61/664,491, filed on Jun. 26, 2012.

(51) Int. Cl.
*A61K 39/395* (2006.01)
*A61K 48/00* (2006.01)

(52) U.S. Cl.
USPC ...................... 424/130.1; 514/44 R

(58) Field of Classification Search
None
See application file for complete search history.

(56) References Cited

U.S. PATENT DOCUMENTS

2003/0073130 A1* 4/2003 Baker et al. ............ 435/7.1
2005/0147555 A1* 7/2005 Fan et al. ............... 424/1.49

FOREIGN PATENT DOCUMENTS

WO   WO 2004/112566   12/2004
WO   WO 2010/065437   6/2010

OTHER PUBLICATIONS

Blumenschein et al (Clinical Cancer Research, 2010, 16: 279-290).*
Astorga and Carlsson, "Hedgehog induction of murine vasculogenesis is mediated by Foxf1 and Bmp4," *Development*, 134(20):3753-3761, 2007.
Ikeya et al., "Gene disruption/knock-in analysis of mONT3: vector construction by employing both in vivo and in vitro recombinations," *International Journal of Developmental Biology*, 49(7):807-823, 2005.
Inomata et al., "Robust stability of the embryonic axial pattern requires a secreted scaffold for chordin degradation," *Cell*, 134:854-865, 2008.
Khankin et al., "Placental vasculature in health and disease," *Semin. Thromb. Hemost.*, 36(3):309-320, 2010.
Langenfeld and Langenfeld, "Bone morphogenetic protein-2 stimulates angiogenesis in developing tumors," *Mol. Cancer Res.*, 2(3):141-149, 2004.
Miljkovic-Licina et al., "Targeting olfactomedin-like 3 inhibits tumor growth by impairing angiogenesis and pericyte coverage," *Molecular Cancer Therapeutics*, 2012.
Moreno-Miralles et al., "New insights into bone morphogenetic protein signaling: focus on angiogenesis," *Curr. Opin. Hematol.*, 16(3):195-201, 2009.
Oelgeschlager et al., "The evolutionarily conserved BMP-binding protein Twisted gastrulation promotes BMP signaling," *Nature*, 405:757-763, 2000.
PCT International Search Report and Written Opinion issued in International Application No. PCT/US2012/048064, mailed Dec. 3, 2012.
Raida et al., "Bone morphogenetic protein 2 (BMP-2) and induction of tumor angiogenesis," *J. Cancer Res. Clin. Oncol.*, 131(11):741-750, 2005.
Rothhammer et al., "Functional implication of BMP4 expression on angiogenesis in malignant melanoma," *Oncogene*, 26(28):4158-4170, 2007.
Smadja et al., "Bone morphogenetic proteins 2 and 4 are selectively expressed by late outgrowth endothelial progenitor cells and promote neoangiogenesis," *Arterioscler. Thromb. Vasc. Biol.*, 28(12):2137-2143, 2008.
Suzuki et al., "Highly efficient transient gene expression and gene targeting in primate embryonic stem cells with helper-dependent adenoviral vectors," *Proc. Natl. Acad. Sci. USA*, 105(37):13781-13786., 2008.
Tomarev and Nakaya, "Highly efficient transient gene expression and gene targeting in primate embryonic stem cells with helper-dependent adenoviral vectors," *Mol. Neurobiol.*, 40(2): 122-38, 2009.
Valdimarsdottir et al., "Stimulation of Id1 expression by bone morphogenetic protein is sufficient and necessary for bone morphogenetic protein-induced activation of endothelial cells," *Circulation*, 106(17):2263-2270, 2002.
Vogt et al., "Bone morphogenetic protein-4 enhances vascular endothelial growth factor secretion by human retinal pigment epithelial cells," *J. Cell Biochem.*, 98(5):1196-1202, 2006.
Winnier et al., "Bone morphogenetic protein-4 is required for mesoderm formation and patterning in the mouse," *Genes Dev.*, 9(17):2105-2116, 1995.
Zeng et al., "hOLF44, a secreted glycoprotein with distinct expression pattern, belongs to an uncharacterized olfactomedin-like subfamily newly identified by phylogenetic analysis," *FEBS Letters*, 571(1-3):74-80, 2004.
Zheng et al., "Fibroblast growth factor 2 is required for maintaining the neural stem cell pool in the mouse brain subventricular zone," *Dev. Neurosci.*, 26(2-4):181-196, 2004.
Zhou et al., "ERK signaling is a central regulator for BMP-4 dependent capillary sprouting," *Cardiovasc. Res.*, 76(3):390-399, 2007.

\* cited by examiner

*Primary Examiner* — Sean Aeder
(74) *Attorney, Agent, or Firm* — Parker Highlander PLLC

(57) ABSTRACT

The present invention relates to antibodies against specific domains of Olfml3 and the use of such in angiogenesis. In particular aspects, angiogenesis-related conditions, such as cancer, can be treated by the composition comprising the Olfml3 antagonists.

15 Claims, 27 Drawing Sheets

A.

B.

A.

murine Olfml3   SIGNAL PEPTIDE (1-22)   COILED COIL (25-101)
MGPSAPLLLLFFLSWTGPLQGQQHRLVEYHERRLAALEPRLAQCQDQASR 50
                                    PEPTIDE A
LAAELRDFKSKKLPLLEVAEKERETLRIDADSISQRVDRLEREVDYLETQ 100

NPALPCVELDEKVTGGPGAKGKGRRNEKYDMVTDCSYTVAQVRSMKILKR 150

FGGSAGLWTKDPLGPAEKIYVLDGTQNDTAFVFPRLRDFTLAMAARKASR 200

IRVPFPWVGTGQLVYGGFLYYARRPPGGPGGGGELENTLQLIKFHLANRT 250
                 OLFACTOMEDIN-LIKE (134-401)
VVDSSVFPAESLIPPYGLTADTYIDLAADEEGLWAVYATRDDDRHLCLAK 300

LDPQTLDTEQQWDTPCPRENAEAAFVICGTLYVVYNTRPASRARIQCSFD 350
                                        PEPTIDE B
ASGTLAPERAALSYFPRRYGAHASLRYNPREROLYAWDDGYQIVYKLEMK 400

KKEEEV 406

B.

Olfml3 peptide A mouse Olfml3 (86-99):  RVDRLEREVDYLET
human Olfml3 (86-99):  RVDRLEREVDYLET
                       **************

Olfml3 peptide B mouse Olfml3 (390-403):  GYQIVYKLEMKKKE
human Olfml3 (390-403):  GYQIVYKLEMKKKE
                         ********:

C. 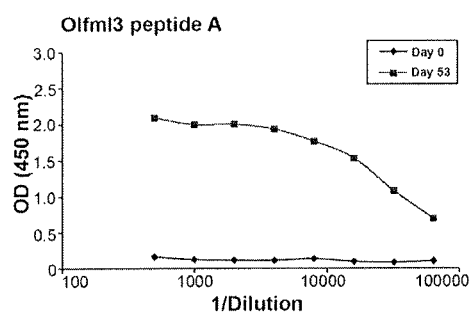

D. 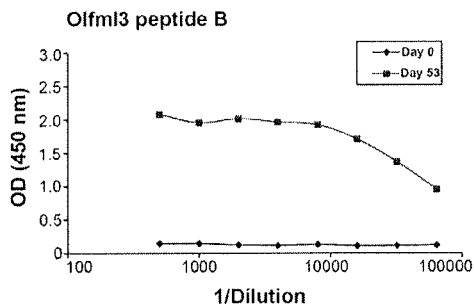

FIGS. 12A-12D

| pH051_FH_mouse | Visible? | Displaying Protein Identification Probability | Acc. No | MW |
|---|---|---|---|---|
| | | Identified Proteins (24) | | |
| 1 | True | Keratin, type II cytoskeletal 1 OS=Mus musculus GN=Krt1 PE=1 SV=4 | P04104 | 66 kDa |
| 2 | True | Keratin, type II cytoskeletal 73 OS=Mus musculus GN=Krt73 PE=2 SV=1 | Q6NXH9 | 59 kDa |
| 3 | True | Keratin, type I cytoskeletal 17 OS=Mus musculus GN=Krt17 PE=1 SV=3 | Q9QWL7 | 48 kDa |
| 4 | True | Keratin, type I cytoskeletal 10 OS=Mus musculus GN=Krt10 PE=1 SV=3 | P02535 | 58 kDa |
| 5 | True | Keratin, type II cytoskeletal 2 epidermal OS=Mus musculus GN=Krt2 | Q3TTY5 | 71 kDa |
| 6 | True | Keratin, type II cytoskeletal 72 OS=Mus musculus GN=Krt72 PE=2 SV=1 | Q6IME9 | 57 kDa |
| 7 | True | Bone morphogenetic protein 4 OS=Mus musculus GN=Bmp4 PE=1 SV=1 | P21275 | 46 kDa |
| 8 | True | Angiotensin-induced protein 3 OS=Mus musculus GN=Arrig2 PE=1 SV=1 | Q8CJ87 | 56 kDa |
| 9 | True | Voltage-dependent anion-selective channel protein 1 OS=... | Q60932 | 32 kDa |
| 10 | True | Anionic trypsin-2 OS=Mus musculus GN=Prss2 PE=2 SV=1 | P07146 | 26 kDa |

FIG. 14

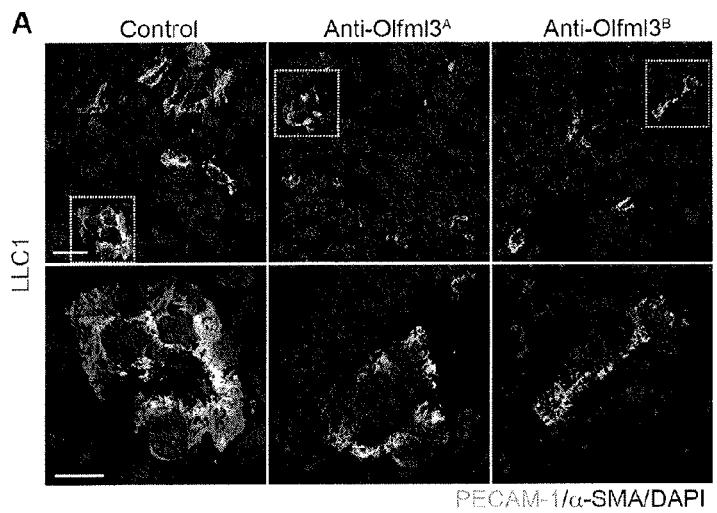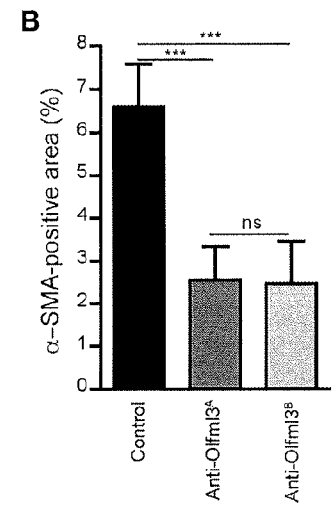
FIGS. 18A-18B
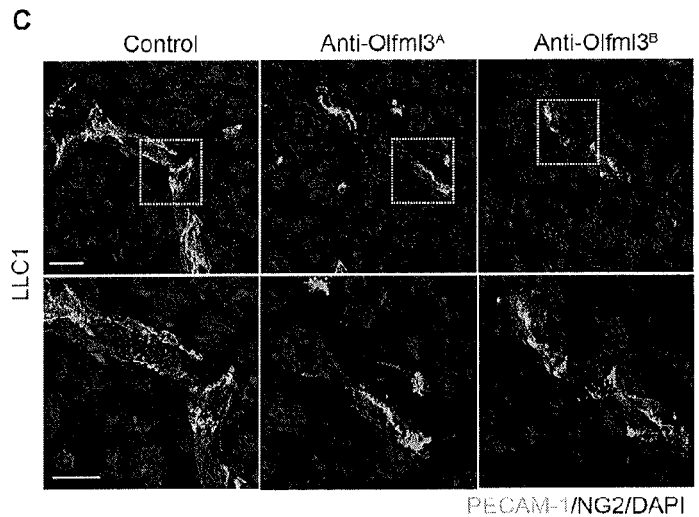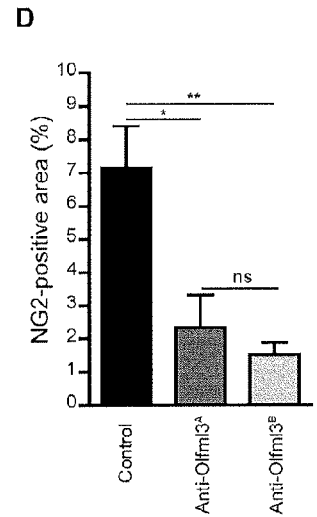
FIGS. 18C-18D

A

Olfml3_mouse (Q8BK62) (UniProtKB/Swiss-Prot)

```
   SIGNAL PEPTIDE (1-22)        COILED-COIL (25-101)
MGPSAPLLLLFFLSWTGPLQGQQHHLVEYHERRLAALEERLAQCQDQSSR  50
                                          PEPTIDE A
LAAVLRDFKNKDLPLLEVAEKEREILRTEAQSISGRVDRLEREVDYLETQ 100

PALPCVELDEKVTGGPGAKGKGRRNEKYDMVTDCSYTVAQVRSMKILKR  150

FGGSAGLWTKDPLGPAEKIYVLDGTQNDTAFVFPRLRDFTLAMAARKASR 200

IRVPFPWVGTGQLVYGGFLYYARRPPGGPGGGELENTLQLIKFHLANRT 250
                 OLFACTOMEDIN-LIKE (134-401)
VVDSSVFPAESLIPPYGLTADTYIDLAADEEGLWAVYATRDDDRHLCLAK 300

LDPQTLDTEQQWDTPCPRENAEAAFVICGTLYVVYNTRPASRARIQCSFD 350
                                          PEPTIDE B
ASGTLAPERAALSYFPRRYGAHASLRYNPREROLYAWDDGYQIVYKLEMK 400

KKEEEV 406
```

B

Olfml3 peptide A

```
mouse Olfml3 (86-99):  RVDRLEREVDYLET
human Olfml3 (86-99):  RVDRLEREVDYLET
                       **************
```

Olfml3 peptide B

```
mouse Olfml3 (390-403): GYQIVYKLEMKKKE
human Olfml3 (390-403): GYQIVYKLEMRKKE
                        **********:***
```

C

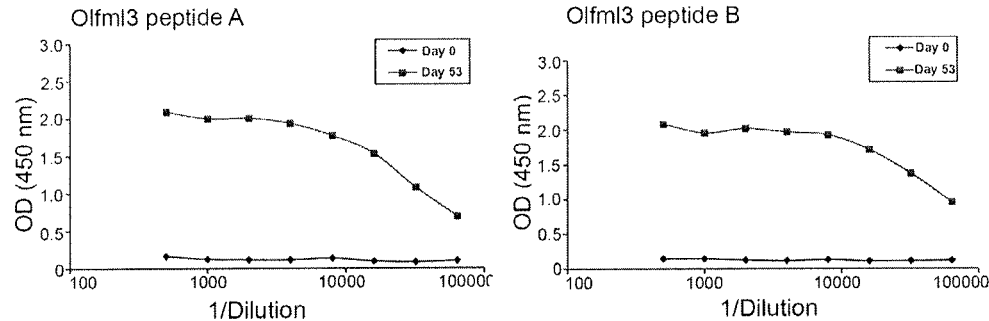

SEQUENCE LISTING

```
<160> NUMBER OF SEQ ID NOS: 16

<210> SEQ ID NO 1
<211> LENGTH: 406
<212> TYPE: PRT
<213> ORGANISM: Homo sapiens

<400> SEQUENCE: 1

Met Gly Pro Ser Thr Pro Leu Leu Ile Leu Phe Leu Leu Ser Trp Ser
1               5                   10                  15

Gly Pro Leu Gln Gly Gln Gln His His Leu Val Glu Tyr Met Glu Arg
            20                  25                  30

Arg Leu Ala Ala Leu Glu Glu Arg Leu Ala Gln Cys Gln Asp Gln Ser
        35                  40                  45

Ser Arg His Ala Ala Glu Leu Arg Asp Phe Lys Asn Lys Met Leu Pro
    50                  55                  60

Leu Leu Glu Val Ala Glu Lys Glu Arg Glu Ala Leu Arg Thr Glu Ala
65                  70                  75                  80
```

```
Asp Thr Ile Ser Gly Arg Val Asp Arg Leu Glu Arg Val Asp Tyr
                85                  90                  95
Leu Glu Thr Gln Asn Pro Ala Leu Pro Cys Val Glu Phe Asp Lys
            100                 105                 110
Val Thr Gly Gly Pro Gly Thr Lys Gly Lys Gly Arg Arg Asn Glu Lys
        115                 120                 125
Tyr Asp Met Val Thr Asp Cys Gly Tyr Thr Ile Ser Gln Val Arg Ser
    130                 135                 140
Met Lys Ile Leu Lys Arg Phe Gly Gly Pro Ala Gly Leu Trp Thr Lys
145                 150                 155                 160
Asp Pro Leu Gly Gln Thr Glu Lys Ile Tyr Val Leu Asp Gly Thr Gln
                165                 170                 175
Asn Asp Thr Ala Phe Val Phe Pro Arg Leu Arg Asp Phe Thr Leu Ala
            180                 185                 190
Met Ala Ala Arg Lys Ala Ser Arg Val Arg Val Pro Phe Pro Trp Val
        195                 200                 205
Gly Thr Gly Gln Leu Val Tyr Gly Gly Phe Leu Tyr Phe Ala Arg Arg
    210                 215                 220
Pro Pro Gly Arg Pro Gly Gly Gly Glu Met Glu Asn Thr Leu Gln
225                 230                 235                 240
Leu Ile Lys Phe His Leu Ala Asn Arg Thr Val Val Asp Ser Ser Val
                245                 250                 255
Phe Pro Ala Glu Gly Leu Ile Pro Pro Tyr Gly Leu Thr Ala Asp Thr
            260                 265                 270
Tyr Ile Asp Leu Ala Ala Asp Glu Glu Gly Leu Trp Ala Val Tyr Ala
        275                 280                 285
Thr Arg Glu Asp Asp Arg His Leu Cys Leu Ala Lys Leu Asp Pro Gln
    290                 295                 300
Thr Leu Asp Thr Glu Gln Gln Trp Asp Thr Pro Cys Pro Arg Glu Asn
305                 310                 315                 320
Ala Glu Ala Ala Phe Val Ile Cys Gly Thr Leu Tyr Val Val Tyr Asn
                325                 330                 335
Thr Arg Pro Ala Ser Arg Ala Arg Ile Gln Cys Ser Phe Asp Ala Ser
            340                 345                 350
Gly Thr Leu Thr Pro Glu Arg Ala Ala Leu Pro Tyr Phe Pro Arg Arg
        355                 360                 365
Tyr Gly Ala His Ala Ser Leu Arg Tyr Asn Pro Arg Glu Arg Gln Leu
    370                 375                 380
Tyr Ala Trp Asp Asp Gly Tyr Gln Ile Val Tyr Lys Leu Glu Met Arg
385                 390                 395                 400
Lys Lys Glu Glu Glu Val
                405

<210> SEQ ID NO 2
<211> LENGTH: 1852
<212> TYPE: DNA
<213> ORGANISM: Homo sapiens

<400> SEQUENCE: 2
caggagagaa ggcaccgccc ccaccccgcc tccaaagcta accctcgggc ttgaggggaa      60
gaggctgact gtacgttcct tctactctgg caccactctc caggctgcca tggggcccag     120 caccccctctc ctcatcttgt tccttttgtc atggtcggga cccctccaag acagcagca     180 ccaccttgtg gagtacatgg aacgccgact agctgcttta gaggaacggc tggcccagtg     240
ccaggaccag agtagtcggc atgctgctga gctgcgggac ttcaagaaca gatgctgcc     300
```

```
actgctggag gtggcagaga aggagcggga ggcactcaga actgaggccg acaccatctc   360
cgggagagtg gatcgtctgg agcgggaggt agactatctg gagacccaga acccagctct   420
gccctgtgta gagtttgatg agaaggtgac tggaggccct gggaccaaag gcaagggaag   480
aaggaatgag aagtacgata tggtgacaga ctgtggctac acaatctctc aagtgagatc   540
aatgaagatt ctgaagcgat tggtggccca gctggtctat ggaccaagg atccactggg    600
gcaaacagag aagatctacg tgttagatgg gacacagaat gacacagcct tgtcttccc    660
aaggctgcgt gacttcaccc ttgccatggc tgcccggaaa gcttcccgag tccgggtgcc   720
cttcccctgg gtaggcacag gcagctggt atatggtggc tttctttatt ttgctcggag    780
gcctcctgga agacctggtg gaggtggtga gatggagaac actttgcagc taatcaaatt   840
ccacctggca accgaacag tggtggacag ctcagtattc ccagcagagg ggctgatccc     900
cccctacggc ttgacagcag acacctacat cgacctggca gctgatgagg aaggtctttg   960
ggctgtctat gccacccggg aggatgcaga gcacttgtgt ctggccaagt tagatccaca  1020
gacactggac acagagcagc agtgggacac accatgtccc agagagaatg ctgaggctgc  1080
ctttgtcatc tgtgggaccc tctatgtcgt ctataacacc cgtcctgcca gtcgggcccg  1140
catccagtgc tcctttgatg ccagcggcac cctgaccct gaacgggcag cactcccta    1200
ttttccccgc agatatggtg cccatgccag cctccgctat aaccccgag aacgccagct    1260
ctatgcctgg gatgatggct accagattgt ctataagctg gagatgagga agaaagagga  1320
ggaggtttga ggagctagcc ttgttttttg catctttctc actcccatac atttatatta  1380
tatccccact aaatttcttg ttcctcattc ttcaaatgtg ggccagttgt ggctcaaatc  1440
ctctatattt ttagccaatg gcaatcaaat tctttcagct cctttgtttc atacggaact  1500
ccagatcctg agtaatcctt ttagagcccg aagagtcaaa accctcaatg ttccctcctg  1560
ctctcctgcc ccatgtcaac aaatttcagg ctaaggatgc cccagaccca gggctctaac  1620
cttgtatgcg ggcaggccca gggagcaggc agcagtgttc ttcccctcag agtgacttgg  1680
ggagggagaa ataggaggag acgtccagct ctgtcctctc ttcctcactc ctcccttcag  1740
tgtcctgagg aacaggactt tctccacatt gttttgtatt gcaacatttt gcattaaaag  1800
gaaaatccac tgctaaaaaa aaaaaaaaaa aaaaaaaaaa aaaaaaaaaa aa          1852
```

<210> SEQ ID NO 3
<211> LENGTH: 406
<212> TYPE: PRT
<213> ORGANISM: Mus musculus

<400> SEQUENCE: 3

```
Met Gly Pro Ser Ala Pro Leu Leu Leu Phe Phe Leu Ser Trp Thr
1               5                   10                  15

Gly Pro Leu Gln Gly Gln Gln His His Leu Val Glu Tyr Met Glu Arg
                20                  25                  30

Arg Leu Ala Ala Leu Glu Glu Arg Leu Ala Gln Cys Gln Asp Gln Ser
            35                  40                  45

Ser Arg His Ala Ala Glu Leu Arg Asp Phe Lys Asn Lys Met Leu Pro
        50                  55                  60

Leu Leu Glu Val Ala Glu Lys Glu Arg Glu Thr Leu Arg Thr Glu Ala
65                  70                  75                  80

Asp Ser Ile Ser Gly Arg Val Asp Arg Leu Glu Arg Glu Val Asp Tyr
                85                  90                  95

Leu Glu Thr Gln Asn Pro Ala Leu Pro Cys Val Glu Leu Asp Glu Lys
                100                 105                 110
```

```
Val Thr Gly Gly Pro Gly Ala Lys Gly Lys Gly Arg Arg Asn Glu Lys
            115                 120                 125

Tyr Asp Met Val Thr Asp Cys Ser Tyr Thr Val Ala Gln Val Arg Ser
        130                 135                 140

Met Lys Ile Leu Lys Arg Phe Gly Gly Ser Val Gly Leu Trp Thr Lys
145                 150                 155                 160

Asp Pro Leu Gly Pro Ala Glu Lys Ile Tyr Val Leu Asp Gly Thr Gln
                165                 170                 175

Asn Asp Thr Ala Phe Val Phe Pro Arg Leu Arg Asp Phe Thr Leu Ala
            180                 185                 190

Met Ala Ala Arg Lys Ala Ser Arg Ile Arg Val Pro Phe Pro Trp Val
        195                 200                 205

Gly Thr Gly Gln Leu Val Tyr Gly Gly Phe Leu Tyr Tyr Ala Arg Arg
    210                 215                 220

Pro Pro Gly Gly Pro Gly Gly Gly Glu Leu Glu Asn Thr Leu Gln
225                 230                 235                 240

Leu Ile Lys Phe His Leu Ala Asn Arg Thr Val Val Asp Ser Ser Val
                245                 250                 255

Phe Pro Ala Glu Ser Leu Ile Pro Pro Tyr Gly Leu Thr Ala Asp Thr
            260                 265                 270

Tyr Ile Asp Leu Ala Ala Asp Glu Glu Gly Leu Trp Ala Val Tyr Ala
        275                 280                 285

Thr Arg Asp Asp Asp Arg His Leu Cys Leu Ala Lys Leu Asp Pro Gln
    290                 295                 300

Thr Leu Asp Thr Glu Gln Gln Trp Asp Thr Pro Cys Pro Arg Glu Asn
305                 310                 315                 320

Ala Glu Ala Ala Phe Val Ile Cys Gly Thr Leu Tyr Val Val Tyr Asn
                325                 330                 335

Thr Arg Pro Ala Ser Arg Ala Arg Ile Gln Cys Ser Phe Asp Ala Ser
            340                 345                 350

Gly Thr Leu Ala Pro Glu Arg Ala Ala Leu Ser Tyr Phe Pro Arg Arg
        355                 360                 365

Tyr Gly Ala His Ala Ser Leu Arg Tyr Asn Pro Arg Glu Arg Gln Leu
    370                 375                 380

Tyr Ala Trp Asp Asp Gly Tyr Gln Ile Val Tyr Lys Leu Glu Met Lys
385                 390                 395                 400

Lys Lys Glu Glu Glu Val
                405

<210> SEQ ID NO 4
<211> LENGTH: 1736
<212> TYPE: DNA
<213> ORGANISM: Mus musculus

<400> SEQUENCE: 4
agagctaacg ggctggaggg aaagaggccg aatgcacaca ctcctctggc cccacttaag      60
gctgccatgg ggcccagtgc tcctctgctg ctcctcttct ttttgtcatg gacgggaccc     120
cttcagggac agcagcacca ccttgtggag tacatggaac gccgactagc tgccttagag     180
gaacggctgg cccaatgcca ggatcagagt agtcggcatg ctgccgagct cgggacttc      240 aaaaacaaga tgttgcctct cctggaggtg gcagagaagg agcgggagac cctcagaact     300
gaagcagact ccatctcagg aagagtggac cgtcttgaaa gggaggtaga ctatctggag     360
acacagaacc cagcttttgcc ctgtgtagag ctggatgaga aggtgactgg aggtcctgga     420
gccaaaggca agggccgaag aaatgagaaa tacgatatgg tgacggactg tagctacaca     480
```

```
gtcgctcagg tgaggtcaat gaagatcctg aagcggtttg gtggttcagt tggcctatgg      540
accaaggatc cgctgggcc agcagagaag atctacgtgt tagacggcac ccagaacgac       600
acggcttttg tcttcccaag gctgcgtgac ttcacccttg ccatggctgc ccggaaagct      660
tcccgaattc gggtgccctt ccctgggta ggcacgggc agctggtgta cgtggcttc        720 ctttattatg ctcgaaggcc tcctggagga cctggagggg gtggtgaatt ggagaacact      780
ctgcagctga tcaaatttca cttggcaaac cgaacagtgg tggatagctc agtgttccct     840
gcagagagcc tgatacccc ctacggcctg acagcagata catatatcga cctggcagct      900
gatgaggagg gcctgtgggc tgtctatgcc actcgagatg atgacaggca tttgtgtcta     960
gccaagttag acccacagac acttgacaca gagcagcagt gggacacacc atgtcccaga    1020
gagaacgcag aggctgcgtt tgtcatctgt gggaccctgt acgttgtcta taacacccgc    1080
cctgccagta gggctcgtat tcagtgttcc ttcgatgcca gtggtactct cgcccctgaa    1140
agggcagcac tctcctattt tccacgccga tatggtgccc atgccagcct tcgctataac    1200
ccccgtgagc gccagctgta tgcctgggat gatggctacc agattgtcta caaattggag    1260
atgaagaaga aggaggagga agtttaagca gctagccttg tgctcttgat tcttatgccc    1320
agacatttat attcctgtga gctctcctgc agttcatcct tcaaaacgaa ggccagtggt    1380
ggtagctcat atacccctaat ttctaaagga caaccaaatt ctcaagcccc tctgttttat    1440
gcagaactcc agatcctggg tagcatttta gaactgaaca gcaaacaaac accctaaatc    1500
ttcactcctg ccttatgtcc acaaagttta gttccaaact cagagccctg tcctttggag    1560
agggtcaacc ccagacagca ggcgacagca ttcttgccct cagtatgacc gaagggagag    1620
aactcagaga caaagctgcc ctccctccct tcccctcca gtgtagggga gaatgggct     1680 ttccccacat cactttgtat ggtaacagtt tgcattaaaa ggaaaaccca ccattc       1736
```

<210> SEQ ID NO 5
<211> LENGTH: 41
<212> TYPE: DNA
<213> ORGANISM: Artificial Sequence
<220> FEATURE:
<223> OTHER INFORMATION: Synthetic primer

<400> SEQUENCE: 5

```
ctaatacgac tcactatagg gatgctcctg gctctgggac t                          41
```

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6

```
tgcagctggt ccccttctat g                                                21
```

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7

```
atgctcctgg ctctgggact c                                                21
```

```
<210> SEQ ID NO 8
<211> LENGTH: 42
<212> TYPE: DNA
<213> ORGANISM: Artificial Sequence
<220> FEATURE:
<223> OTHER INFORMATION: Synthetic primer

<400> SEQUENCE: 8
ctaatacgac tcactatagg gtgcagctgg tcccttcta tg                              42

<210> SEQ ID NO 9
<211> LENGTH: 42
<212> TYPE: DNA
<213> ORGANISM: Artificial Sequence
<220> FEATURE:
<223> OTHER INFORMATION: Synthetic primer

<400> SEQUENCE: 9
ctaatacgac tcactatagg gagtgctcct ctgctgctcc tc                             42

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
cgtgtcgttc tgggtgccgt c                                                   21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
agtgctcctc tgctgctcct c                                                   21

<210> SEQ ID NO 12
<211> LENGTH: 42
<212> TYPE: DNA
<213> ORGANISM: Artificial Sequence
<220> FEATURE:
<223> OTHER INFORMATION: Synthetic primer

<400> SEQUENCE: 12
ctaatacgac tcactatagg gcgtgtcgtt ctgggtgccg tc                             42

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
gctgtctatg ccactcgaga tg                                                  22

<210> SEQ ID NO 14
<211> LENGTH: 24
<212> TYPE: DNA
<213> ORGANISM: Artificial Sequence
<220> FEATURE:
<223> OTHER INFORMATION: Synthetic primer
```

```
<400> SEQUENCE: 14
tgtgtcaagt gtctgtgggt ctaa                                              24

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
gtctatgcca cccgggagga t                                                 21

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
tgtgtccagt gtctgtggat ctaa                                              24
```

METHODS AND COMPOSITIONS FOR MODULATION OF OLFML3 MEDIATED ANGIOGENESIS

This application claims benefit of priority to U.S. Provisional Application Ser. No. 61/515,669, filed Aug. 5, 2011 and U.S. Provisional Application Ser. No. 61/664,491, filed Jun. 26, 2012, the entire contents of which are hereby incorporated by reference.

BACKGROUND OF THE INVENTION

1. Field of the Invention

The present invention relates generally to the fields of molecular biology and oncology. More particularly, it concerns compositions comprising binding molecules for Olfml3, an angiogenesis modulator, and associated methods of treating angiogenesis-related conditions.

2. Description of Related Art

Angiogenesis is a multi-step cellular process of capillary sprouting and formation of neo-vasculature from preexisting blood vessels. The complex process involves disassembly of endothelial junctions, followed by endothelial cells detachment, proliferation and migration as well as subsequent re-establishment of intercellular and cell-matrix contact. As such it requires coordinated actions of a variety of vascular cell adhesion molecules and growth factors originating from endothelial cells themselves or neighboring mural cells. Indeed, angiogenesis is a tightly tuned process regulated by pro- and anti-angiogenic factors (Folkman, 1995).

Numerous studies have demonstrated that excessive angiogenesis influences significantly various disease states including tumor growth, ischemic cardiovascular pathologies or chronic inflammatory diseases (Carmeliet, 2003; Carmeliet, 2005; Gariano and Gardner, 2005).

From vascular mediated pathologies, tumor-associated angiogenesis is the most extensively studied. It was first postulated that tumors cannot grow further than a size of 2-3 mm$^3$ in the absence of neovascularization (Folkman, 1971). Therefore, angiogenesis is a prerequisite for tumor growth and blocking this process can prevent further proliferation of tumor cells. Furthermore, prevention of angiogenesis targets normal tissue and does not escape therapy by mutagenesis as seen with tumor cells. It is thus expected that anti-angiogenic therapy be better sustained in keeping tumor growth under control than any other treatment directly addressing tumor cells. Despite the fact that vascular endothelial cell growth factor (VEGF), fibroblast growth factor (FGF) and other pro-angiogenic molecules are indispensable for vessel formations (Hanahan, 1997; Yancopoulos et al., 2000), the complete molecular and cellular mechanisms governing tumor-associated angiogenesis are poorly understood.

In addition, diseases complicated by vascular leakage and/or neovascularization in the eye are responsible for the vast majority of visual morbidity and blindness in developed countries. Retinal neovascularization occurs in ischemic retinopathies such as diabetic retinopathy and is a major cause of visual loss in working age patients (Klein et al., 1984). Choroidal neovascularization occurs as a complication of age-related macular degeneration and is a major cause of visual loss in elderly patients (Ferris et al., 1984). Improved treatments are needed to reduce the high rate of visual loss, and their development is likely to be facilitated by greater understanding of the molecular pathogenesis of ocular neovascularization.

Therefore, there remains a need to develop novel methods for targeting novel vascular molecules expressed and/or secreted by angiogenic cells.

SUMMARY OF THE INVENTION

Olfml3 protein is discovered to be a proangiogenic, endothelial cell-derived factor that interacts with BMP4 and promotes tumor angiogensis. Specific Olfml3 inhibitors may be useful for angiogensis inhibition, especially in pathological angiogenic conditions. In accordance with certain aspects of the present invention, there may be provided a method of inhibiting angiogenesis in a subject having an angiogenic condition. The method may comprise administering to the subject a composition comprising an antibody or a nucleic acid encoding the antibody, wherein the antibody recognizes and binds to at least one amino acid sequence on an Olfml3 protein. For example, the amino acid sequence may be defined by (i) amino acid positions 86-403, (ii) amino acid positions 86-99, (iii) amino acid positions 114-143, or (iv) amino acid positions 390-403 of SEQ ID NO:1 (human Olfml3 protein) or SEQ ID NO:3 (mouse Olfml3 protein). In a particular aspect, the antibody may inhibit the binding of an Olfml3 protein to BMP4 protein.

In a certain aspect, the subject has tumor. The antibody may reduce the number of pericytes in vessels associated with the tumor. In a further aspect, the antibody may reduce the tumor size.

In a further aspect, there may be provided a method of inhibiting angiogenesis in a cell comprising inhibiting the binding of Olfml3 protein to BMP4 protein. For example, the binding of Olfml3 protein to BMP4 protein may be inhibited through a polypeptide that binds to Olfml3 at a position which BMP4 protein normally binds to thereby inhibit the binding of BMP4 thereto. The cell may be located in a subject having an angiogenic condition. The method may further comprise administering to the subject a composition comprising an antibody that inhibits the binding between Olfml3 protein and BMP4 protein, or a nucleic acid encoding the antibody. For example, the antibody may recognize and bind to an amino acid sequence defined by (i) amino acid positions 86-403, (ii) amino acid positions 86-99, (iii) amino acid positions 114-143, or (iv) amino acid positions 390-403 of SEQ ID NO:1 (human Olfml3) or SEQ ID NO:3 (mouse Olfml3).

The antibody may be a monoclonal antibody, a polyclonal antibody, a chimeric antibody, an affinity matured antibody, a humanized antibody, a human antibody or an antibody fragment. Particularly, the antibody is a monoclonal antibody, polycolonal antibody or a humanized antibody. The antibody fragment may be Fab, Fab', Fab'-SH, F(ab')$_2$, or scFv.

For medical or clinical applications, the antibody may be attached to an agent to be delivered to an angiogenic cell or targeted to an Olfml3-expressing cell. The agent may be a cytotoxic agent, a cytokine, an anti-angiogenic agent, a chemotherapeutic agent, a diagnostic agent, an imaging agent, a radioisotope, a pro-apoptosis agent, an enzyme, a hormone, a growth factor, a peptide, a protein, an antibiotic, an antibody or fragment thereof, an imaging agent, an antigen, a survival factor, an anti-apoptotic agent, a hormone antagonist, a virus, a bacteriophage, a bacterium, a liposome, a microparticle, a magnetic bead, a microdevice, a cell, a nucleic acid or an expression vector.

There may also be provided a pharmaceutical composition comprising one or more nucleic acids or the antibody described above in a pharmaceutically acceptable carrier, for example, a pharmaceutical composition comprising the antibody or fragment and a pharmaceutically acceptable carrier or a pharmaceutical composition comprising one or more nucleic acids described above and a pharmaceutically acceptable carrier.

The pharmaceutical composition of the present invention may further comprise a lipid component, which is believed to likely give the nucleic acid or antibody an improved stability, efficacy and bioavailability, with perhaps even reduced toxicity. The lipid component may form a liposome, but this is not believed to be required. In certain aspects, the composition further comprises cholesterol or polyethyleneglycol (PEG).

Exemplary lipids include, but are not limited to, 1,2-dioleoyl-sn-glycero-3-phosphatidylcholine (DOPC), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, dilinoleoylphosphatidylcholine distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), lysophosphatidylethanolamine, phosphatidylserine, phosphatidylglycerol, dimyristoyl phosphatidylserine ("DMPS"), dipalmitoyl phosphatidylserine ("DPPS"), brain phosphatidylserine ("BPS"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), dioleoylphosphatidylglycerol ("DOPG"), cholesterol or polyethyleneglycol (PEG).

It is contemplated that the Olfml3 inhibitory molecules, the antibody or the composition described above may be used in the treatment of any disease or disorder in which angiogenesis plays a role, which will be referred to generally as an angiogenesis-related condition. It is contemplated that the invention will find applicability in any such disorder in subjects such as humans or animals. Exemplary angiogenesis-related conditions include an ocular neovascularization, an arteriovenous malformation, coronary restenosis, peripheral vessel restenosis, glomerulonephritis, rheumatoid arthritis, pancreatitis, a bowel disease, an ischemic cardiovascular pathology, or a chronic inflammatory disease.

In the case of cancer, exemplary angiogenic cancers include breast cancer, lung cancer, prostate cancer, ovarian cancer, brain cancer, liver cancer, cervical cancer, colorectal cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. Ocular neovascularization disorders may include macular degeneration (e.g., age-related macular degeneration (AMD), corneal graft rejection, corneal neovascularization, retinopathy of prematurity (ROP) and diabetic retinopathy.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one. The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Validation of data obtained by microarray analysis using quantitative real-time reverse transcrption-polymerase chain reaction (RT-PCR). Bars represent the quantity of the Olfml3 mRNA (relative units) in total RNA isolates from t.End.1V$^{high}$ and t.End.1V$^{high}$ cells. Values for each sample were normalized to values of mouse β-actin, β-tubulin and/or EEFJA genes according to the GeNorm method (Vandesompele et al., 2002). Relative values from individual experiments were averaged and plotted with standard deviation (SD) as error bars. The statistical analysis was performed using the paired t-test (p=0.00918). FIG. 1B. Western blotting shows the differential expression of Olfml3 protein in angiogenic (t.End.1V$^{high}$) versus resting (t.End.1V$^{low}$) endothelial cells.

FIG. 2A. Immunostaining on human placental villi at a term pregnancy. Parafine sections were incubated with the rabbit anti-Olfml3 antibody detected using a biothinylated anti-rabbit antibody (brown). Staining illustrates that Olfml3 is expressed by endothelial cells of placental angiogenic vessels. H&E: hematoxylin and eosin stain; by: blood vessels. Bars corresponds to 20× (upper panels) and 40× magnification (lower panels). FIG. 2B. Left panel: Double in situ mRNA hybridization on angiogenic vessels (arrowheads) immigrated into bFGF-loaded matrigel plugs (mg). Cryosections were incubated with Olfml3 anti-sense RNA probes (green) and PECAM-1 anti-sense RNA probes (red). Double labeling illustrates that Olfml3-expressing cells are PECAM-1 positive (merge). No staining observed in the control, cryosections incubated with Olfml3 and Pecam1 sense probes (lower panel). Right panel: Double immunofluorescence on angiogenic vessels immigrated into bFGF-loaded matrigel plugs (mg). Cryosections were incubated with rabbit anti-Olfml3 antibody detected by donkey anti-rabbit IgG (red) and rat anti-PECAM-1 antibody detected by donkey anti-rat IgG (green). Double labeling illustrates that Olfml3-expressing cells are PECAM-1 positive (merge). No staining observed in the control, cryosections incubated with Olfml3 preimmune sera (lower panel). FIG. 2C. Left panel: Double in situ mRNA hybridization on angiogenic vessels (arrowheads) migrated into LLC1 tumors. Cryosections were incubated with Olfml3 RNA probes (green) and PECAM-1 RNA probes (red). Double labeling illustrates that Olfml3-expressing cells are PECAM-1 positive (merge). Surrounding pericytes express low levels of Olfml3 as well (stars). No staining observed in the controls incubated with sense probes (lowest panel). Right panel: Double immunofluorescence on angiogenic vessels migrated into LLC1 tumors. Cryosections were incubated with rabbit anti-Olfml3 antibody (red) and rat anti-PECAM-1 antibody (green). Double labeling illustrates that Olfml3-expressing cells are PECAM-1 positive (merge). Pericytes indicated by stars. TO-PRO dye was used for nuclear staining (blue, B-C). Representative single-frame confocal images are shown. Bars correspond to 20 µm (B and C, upper and lower panels) and 10 µm (B and C, middle panels).

FIG. 3A. Triple immunofluorescence on angiogenic vessels in LLC1 tumors. Cryosections were incubated with rabbit anti-Olfml3 detected by donkey anti-rabbit IgG (light blue), rat anti-PECAM-1 detected by donkey anti-rat IgG (green) and mouse anti-α-SMA detected by goat anti-mouse $IgG_{2a}$ (red). Triple labelling illustrates that Olfml3-expressing endothelial cell (light blue, arrowhead) are PECAM-1 positive (green) and covered by immature, α-SMA-positive mural cells (red). FIG. 3B. Triple immunofluorescence on angiogenic vessels in LLC1 tumors. Cryosections were incubated with rabbit anti-Olfml3 detected by donkey anti-rabbit IgG (light blue), rat anti-PECAM-1 detected by donkey anti-rat IgG (green) and mouse anti-NG2 detected by donkey anti-mouse IgG (red). Triple labelling illustrates that PECAM-1 positive endothelial cells (green) that are covered by mature, NG2-positive mural cells (red) express Olfml3 at very low level (light blue). DAPI nuclear counterstain was used (blue; A-C). Representative single-frame confocal images are shown. Bars correspond to 20 µm (upper and lower panels) and 10 µm (middle panels).

FIG. 4A. Examples of monolayer cultures of t.End.1V$^{high}$ cells silenced for either mock; control siRNA (ctrl siRNA, 0.5 µM), or Olfml3 (Olfml3 siRNA 3, 0.5 µM). Confluent cell monolayers were wounded with a pipette tip (yellow area), and wounded areas were illustrated using an imaging program (yellow area). Cells at the edge of the wound migrated into the wounded area, shown after 16 hours (violet area). FIG. 4B. Distance of migration (µm) was calculated. The progress of wound closure was significantly delayed in the Olfml3-siRNA-silenced cells compared with mock or control siRNA-treated cells. Bars represent means±SD of nine independent culture wells; in total, 3 experiments were performed. FIG. 4C. Reduced migratory ability of Olfml3-silenced t.End.1V$^{high}$ cells was rescued by coating of recombinant Olfml3 protein (+) in vitro, when compared to the t.End.1V$^{high}$ cells cultured on non-coated control plates (−). FIG. 4D. Reduced migratory ability of Olfml3-silenced t.End.1V$^{high}$ cells was rescued by addition of recombinant Olfml3 protein in vitro, when compared to the t.End.1V$^{high}$ cells cultured on control plates (−). FIG. 4E. When coated on culture plates, recombinant Olfml3 promoted t.End.1V$^{high}$ cell migration in the concentration-dependent manner (1-5 ng/µl), when compared to non-coating control (no coat). The statistical analysis using one-way ANOVA with Bonferroni post hoc test was performed.

FIG. 5A. In 3D fibrin gels, control siRNA-treated t.End1.V$^{high}$ cells first send out spikes after 24 h of culture (ctrl siRNA, arrows, 24-32 h). This process continues by sprouting, cell-cell contact formation, which leads to branching of the proliferating cells forming a polygonal network (ctrl siRNA, arrows, 48-72 h). Olfml3 siRNA 3 (0.5 µM) delayed (arrowheads) sprout formation by 48 h (arrowheads). FIG. 5B. Quantification of sprout-forming t.End.1V$^{high}$ cells at early time points (24 h and 32 h) of sprouting assay. Olfml3-siRNA (0.5 µM) treated t.End.1V$^{high}$ cells reduced the total number of sprout-forming cells. The mean and standard deviation of three experiments is shown. The statistical analysis using one-way ANOVA with Bonferroni post hoc test was performed. FIG. 5C. Total length of vascular cords representing the capillary-like network was quantified using MetaMorph software. Length and complexity of the vascular network (cords) of Olfml3-silenced cells is reduced in comparison to control siRNA-transfected cells (top panel) at 72 h. Measurement of total length of the vascular network after Olfml3 silencing (Olfml3 siRNA 3, 0.5 µM) compared to mock- and control siRNA (ctrl siRNA, 0.5 µM)-transfected cells. Eror bars=SD. The statistical analysis using one-way ANOVA with Bonferroni post-hoc test was performed.

FIG. 6A. Macroscopic aspects of 9-days-old tumors grown in mice treated with control, total rabbit IgG or anti-Olfml3 antibody. Bar represent 0.5 cm. Mice treated with anti-Olfml3 antibodies showed reduced tumor weight compared to controls (FIG. 6B). n=5; two tumors per mouse), p<0.05. Stastistical differences compared to control group, calculated by one-way ANOVA tests with Bonferroni post-hoc test. FIG. 6C. Macroscopic aspects of 9-days-old tumors grown in mice treated with control, total rabbit IgG or Olfml3 antibody affinity-purified against either Olfml3 peptide a or b. FIG. 6D. Mice treated with either anti-Olfml3 antibody showed reduced tumor weight compared with controls. Control IgG (n=3; two tumors per mouse), anti-Olfml3 A (n=4; two tumors per mouse), anti-Olfml3 B (n=4; two tumors per mouse). p<0.01 and p<0.001, respectively. Statistical differences compared to control group, calculated by one-way ANOVA tests with Bonefferoni post-hoc test. Scale bar represents 0.5 cm. FIG. 6E. Immunofluorescence analysis of LLC1 tumors treated with control (ctrl IgG) or Olfml3 antibodies (anti-Olfml3) using anti-PECAM-1 antibody (green). DAPI was used as a nuclear counterstain (blue). Representative single-frame confocal images are shown (63× magnification). Bars correspond to 20 µm. FIG. 6F. Quantification of the vascularization level between control (ctrl IgG) and anti-Olfml3 treated tumors was measured as a ratio of the PECAM-1 (green) to DAPI nuclear stain (blue) cells. p<0.01. In each group, quantification was determined by 10 fields in the three different planes per tumor, followed by averaging the values for 10 tumors.

FIG. 7A. Binding of recombinant Olfml3-FLAG to the recombinant BMP4 was detected by enzyme linked immunosorbent assay (ELISA) using FLAG (M2) antibody. The Olfml3-FLAG specifically recognized BMP4 but not BMP1 or BMP9 in a dose-dependent fashion (0.1-1 ng/μl). Negative control was human JAM-C-FLAG recognized by the anti-JAM-C antibody D33. FIG. 7B. Immobilized Olfml3 FLAG-tagged protein on M2 beads binds recombinant BMP4 (21 kDa). Silver-stained SDS gel: lane 1) MW—molecular weight marker, lane 2) directly loaded BMP4 (BMP4); lane 3) pull down of recombinant BMP4 by M2 beads; lane 4) pull down using Olfml3 FLAG-tagged protein and recombinant BMP4 by M2 beads (M2+Olfml3-FLAG+BMP4). FIG. 7C. Blocking of the binding specificity of the rOlfml3-FLAG to recombinant BMP4 protein was detected by enzyme linked immunosorbent assay (ELISA) using Olfml3 antibodies. Binding of Olfml3-FLAG to recombinant BMP4 could be reduced up to 50% using Olfml3 antibody against Olfml3 peptides A+B, A or B (86-99 and 390-403, respectively). FIG. 7D. Blocking of Olfml3-FLAG binding to recombinant BMP4 protein was detected by ELISA using Olfml3 antibodies. Binding of Olfml3-FLAG to recombinant BMP4 could be reduced using Olfml3 antibody against peptides A+B and commercial antibodies against peptide D (Abcam, 114-143), while commercial antibodies against peptide S (Sigma, 46-60) showed no blocking effect.

FIG. 8A. HUVEC were treated with VEGF (50 ng/ml), BMP4 (50 ng/ml) or VEGF+Olfml3 (50 ng/ml+100 ng/ml) for 35 min. Densitometric analysis showed significant increase of ERK tyrosin phosphorylation in HUVECs treated with both BMP4 and Olfml3 together but not in control cells or cells trested with single growth factors. Total ERK serves as a loading control. Each graph value represents the mean of three determinations; error bars, SD. Stastistical differences compared to control group, calculated by one-way ANOVA tests with Bonfferoni post-hoc test. FIG. 8B. Effects of VEGF (50 ng/ml) and BMP4 (50 ng/ml) on the Olfml3 protein expression in HUVECs. HUVEC were cultured for 24 h in the absence or presence of VEGF and BMP4 and subjected to Western blotting using Olfml3 antibody. Quantitative values of Olfml3 protein expression were normalized by the amounts of β-actin protein, and results were given as relative density of the Olfml3/Actin protein ratio. Each value represents the mean of three determinations; error bars, SD. Statistical differences compared to control group, calculated by one-way ANOVA tests with Bonefferoni post-hoc test.

FIGS. 12A-12D. Peptide sequences used for generation of the Olfml3 antibodies. FIG. 12A. Comparison of human and mouse Olfml3 sequences showed complete homology in the protein regions used for generation of the Olfml3 antibodies. Olfml3 peptide A comprises epitopes in the coiled-coil domain of Olfml3 and peptide B in the Olfactomedin-like domain. FIG. 12B. Peptide sequences used for generation of the Olfml3 antibodies. Mouse sequences were identical with human Olfml3. FIG. 12C-12D. Immunoreactivity of the rabbit anti-serum 928 009 against the peptides A (FIG. 12C; left panel) and B (FIG. 12D; right panel).

FIG. 14. Pull down of BMP4 by immobilized Olfml3-FLAG protein. BMP4 was identified in an SDS gel slice by tandem mass spectrometry and displayed as a table using Scaffold software. Detailed results detect BMP4 and false-positive proteins (keratins). Analysis of the peptide and spectra evidence supported the identification of mouse BMP4 as a binding partner of recombinant Olfml3.

FIG. 15A, in situ mRNA hybridization of LLC1 tumors with Olfml3 (green) and PECAM-1 (red) RNA probes shows Olfml3 expression on tumor vessels (arrows) and vessel-associated pericytes (insets, stars). No staining with sense Olfml3 RNA probe (sense). Olfml3-expressing endothelial cells (anti-sense) are PECAM-1$^+$ (overlay). Pericytes express Olfml3 but not PECAM-1 (insets, stars). Bars correspond to 30 μm and 5 μm (insets). FIG. 15B, Olfml3 (red) and PECAM-1 (green) immunostaining of LLC1 tumors shows Olfml3 expression on tumor vessels (arrows) and accompanying pericytes (overlay/inset, stars). Pericytes express Olfml3 but not PECAM-1 (insets, stars). Bars correspond to 30 and 10 μm (inset). FIG. 15C, Olfml3 (light blue), PECAM-1 (green) and α-SMA (red) immunostaining of LLC1 tumors shows Olfml3 expression on tumor vessels and accompanying pericytes (arrows). No Olfml3 staining on α-SMA$^-$ cells (stars). FIG. 15D, Olfml3 (light blue), PECAM-1 (green) and NG2 (red) immunostaining of LLC1 tumors shows Olfml3 expression on tumor vessels and accompanying pericytes (arrows). DAPI—nuclear counterstain (blue) (overlays; FIGS. 15A-D). Bars correspond to 20 μm (FIGS. 15C, D). FIG. 15E, relative Olfml3 mRNA levels in activated R-SMCs versus resting S-SMCs quantified by RT-qPCR. Error bars represent±SD (2 experiments, each group in triplicates); ***P<0.001.

FIG. 16A, Top: in vitro migration assays using mock, control siRNA (ctrl siRNA, 0.5 μM) or Olfml3 siRNA-treated (Olfml3 siRNA, 0.5 μM) t.End.1V$^{high}$ cells. Confluent cell monolayers were wounded (yellow area). Cells migrated into the wounded area after 16 hours (violet area). Bottom: quantification of migration distance (μm) of mock, control- or Olfml3 siRNA-treated t.End.1V$^{high}$ cells. FIG. 16B, rescued migratory ability of Olfml3-silenced t.End.1V$^{high}$ cells on rOlfml3-FLAG-coated plates (1 μg/mL) when compared with non-coated control (0 μg/mL). FIG. 16C, coated rOlfml3-FLAG promotes t.End.1V$^{high}$ cell migration in a concentration-dependent manner (1-5 μg/mL) compared with non-coated control (0 μg/mL). FIG. 16D, in vitro t.End.1V$^{high}$ sprouting assays in 3D-fibrin gels. Control siRNA-treated cells start sprouting after 24 hours (arrows) to form a vascular-like network (32-72 hours). Targeting Olfml3 delays sprouting (arrowheads) by 32 hours (arrows). Bar corresponds to 10 μm. FIG. 16E, quantification of sprout-forming t.End.1V$^{high}$ cells at early-time points (24, 32 hours). Olfml3 targeting (Olfml3 siRNA) reduces the total number of sprouting cells compared with mock or control siRNA-treated cells. FIG. 16F, quantification of total length of vascular-like network of t.End.1V$^{high}$ cells treated with mock, control or Olfml3 siRNAs, normalized to total number of cells/condition. At later time points (48, 72 hours), targeting Olfml3 reduces the length of the vascular-like network compared with controls. Error bars represent ±s.d. (5 experiments; each group in triplicates; FIGS. 16A-C, E, F). *P<0.05; P<0.01; *P<0.001; ns—non significant (FIGS. 16A-C, E, F).

FIG. 17A, 9-day-old LLC1 tumors in mice treated with rabbit IgG (control), or anti-Olfml3$^{A+B}$. Bar represents 1 cm. FIG. 17B, reduced tumor weight in mice treated with anti-Olfml3$^{A+B}$ compared with control IgG-treated tumors. Error bars represent ±SEM (3 experiments; 4-5 mice/group; 2 tumors/mouse). *P<0.05. FIG. 17C, 9-day-old tumors in mice treated with rabbit IgG (control), anti-Olfml3$^{A}$ or anti-Olfml3$^{B}$. Bar represents 1 cm. FIG. 17D, reduced tumor weight in mice treated with either anti-Olfml3$^{A}$ or anti-Olfml3$^{B}$ compared with control IgG-treated tumors. Error bars represent ±SEM (2 experiments; 4-5 mice/group; 2 tumors/mouse). *P<0.05 P<0.01, ns—non significant. FIG. 17E, representative confocal images compare the dense vasculature (PECAM-1, green) of tumors under baseline condition (control) and pruned vasculature after treatments with anti-Olfml3$^{A}$ or anti-Olfml3$^{B}$. DAPI-nuclear counterstain (blue). Bars correspond to 20 μM. FIG. 17F, relative vascular area in tumors treated with total IgG (control), anti-Olfml3$^{A}$ or anti-Olfml3$^{B}$ measured as a ratio of the total pixel count of PECAM-1 to DAPI. Ten individual images at three planes analyzed in 8-10 tumors/group. Error bars represent ±SEM (2 experiments; 4-5 mice/group; 2 tumors/mouse). P<0.01; ***P<0.001.

FIGS. 18A-D. Anti-Olfml3 antibody tumor treatment inhibits pericyte association with vessels. FIG. 18A, top: the abundance of pericytes (α-SMA, red) in LLC1 tumors under baseline condition (control) and after treatment with anti-Olfml3$^{A}$ or anti-Olfml3$^{B}$. Bottom: insets of top panels at higher magnification. FIG. 18B, quantification of pericyte area in LLC1 tumors treated under baseline condition (control) or with anti-Olfml3$^{A}$ or anti-Olfml3$^{B}$. Relative α-SMA$^{+}$ area measured as a ratio of the total pixel count of α-SMA (red) to DAPI (blue). FIG. 18C, top: the abundance of pericytes (NG2, red) in tumors under baseline condition (control) and after treatment with anti-Olfml3$^{A}$ or anti-Olfml3$^{B}$. Bottom: insets of top panels at higher magnification. DAPI (blue)-nuclear counterstain (FIGS. 18A, C). FIG. 18D, relative NG2 area in tumors treated under baseline condition (control) or with anti-Olfml3$^{A}$ or anti-Olfml3$^{B}$ measured as a ratio of the total pixel count of NG2 (red) to DAPI (blue). Ten individual images at three planes analyzed in 8-10 tumors/group (FIGS. 18B, D). Error bars represent ±SEM (2 experiments; 4-5 mice/group; 2 tumors/mouse; FIGS. 18B, D). P<0.01; *P<0.001; ns-non significant (FIGS. 18B, D). Bars correspond to 20 μm (top panels; FIGS. 18A, C) and 10 μm (bottom panels; FIGS. 18A, C).

FIG. 19A, binding of rOlfml3-FLAG to rBMP4 detected by ELISA using FLAG (M2) antibody. The rOlfml3-FLAG specifically recognizes BMP4 but not BMP1 or BMP9 in a dose-dependent manner (0.1-1 μg/mL). Human JAM-C-FLAG-negative control (0.1 μg/mL). FIG. 19B, immobilized rOlfml3-FLAG on M2-beads binds rBMP4. Silver-stained SDS gel: left, input of rBMP4 loaded for comparison (rBMP4; 21 kDa); middle, pull-down of rBMP4 by M2-beads; right, pull-down of rOlfml3-FLAG and rBMP4 by M2-beads (arrow). FIG. 19C, Olfml3 domains relative to anti-Olfml3$^{A}$, anti-Olfml3$^{B}$ and commercial anti-Olfml3$^{C}$ epitope regions. FIG. 19D, blocking of rOlfml3-FLAG binding to rBMP4 by anti-Olfml3$^{A+B}$ (A+B), anti-Olfml3$^{A}$ (A) or anti-Olfml3$^{B}$ (B). FIG. 19E, blocking of rOlfml3-FLAG binding to rBMP4 by anti-Olfml3$^{A±B}$, but not by anti-Olfml3$^{C}$. Error bars represent ±SD (5 experiments; each group in triplicates; FIGS. 19D, E). *P<0.05; ***P<0.001; ns—non significant (FIGS. 19D, E).

FIG. 20A, Olfml3 induces nuclear translocation of SMAD1/5/8. SMAD1 (red) immunostaining compares SMAD1 cytoplasmic localization under baseline conditions (control) with SMAD1 nuclear translocation in HUVECs treated with rOlfml3-FLAG (Olfml3; 100 ng/mL); rBMP4 (BMP4; 50 ng/mL), or combination (Olfml3+BMP4) for 15 minutes. FIG. 20B, Olfml3 induces SMAD1/5/8 phosphorylation in HUVECs. PhosphoSMAD1/5/8 immunostaining (red) compares low levels of phoshoSMAD1/5/8 under control conditions (control: FLAG peptide) and high levels of phosphoSMAD1/5/8 in HUVECs treated with rOlfml3-FLAG (Olfml3; 100 ng/mL), rBMP4 (BMP4; 50 ng/mL) or combination (Olfml3+BMP4) for 15 min. Olfml3 does not induce phosphoSMAD1/5/8 in the presence of anti-Olfml3A+B (Olfml3+anti-Olfml3) compared with control (Olfml3+IgG). FITC-phalloidin staining (green) allows visualization of the cell scaffolds (FIGS. 20A, B). DAPI (blue)-nuclear counterstain (FIGS. 20A, B). Scale bars represent 10 μm (FIGS. 20A, B). FIG. 20C, quantification of the intensity of nuclear phosphoSMAD1/5/8 signals. The combination of the rOlfml3-FLAG and rBMP4 (Olfml3+BMP4) shows an additive effect on SMAD1/5/8 phosphorylation. Mean nuclear intensity was measured from 5-10 random fields/group in 2 experiments. ***P<0.001; ns-non significant. FIG. 20D, prolonged effect on SMAD1/5/8 phosphorylation using both recombinant proteins (Olfml3+BMP4), compared to the effect of rOlfml3-FLAG alone. HUVECs were treated with control (0 min); rOlfml3-FLAG (100 ng/mL) or rOlfml3-FLAG and rBMP4 (Olfml3+BMP4; 100 and 50 ng/mL, respectively) for 15, and 45 minutes and blotted with pSMAD1/5/8 and SMAD1 antibodies.

FIG. 21A, relative Olfml3 mRNA levels in angiogenic endothelial cells that form aggressive hemangiomas in vivo (t.End.1Vhigh) (Hanahan and Weinberg, 2011; Potente et al., 2011), when compared with their resting counterparts (t.End.1 Vlow), quantified by RT-qPCR. Bars represent mean+SD (3 experiments, each group in triplicates); **P<0.01. FIG. 21B, Olfml3 expression in angiogenic blood vessels (bv) of FGF2-loaded matrigel plugs (mp). Representative confocal images of Olfml3 (red) and PECAM-1 (green)

immunostaining of matrigel plugs are shown. White dotted lines indicate the margins of matrigel plugs. Olfml3-expressing endothelial cells are PECAM-1+ (overlay). Scale bar represents 20 μM. FIG. 21C, relative Olfml3 expression levels in primary lung microvascular endothelial cells (LMECs), lung tissue and LLC1 tumor cells. Expression of mouse Olfml3 and reference genes were analyzed by real-time qPCR. LMECs were used as a negative and lung tissue as a positive control for Olfml3 expression (Crawford and Ferrara, 2009). LLC1 tumor cells did not express Olfml3 mRNA. The values were normalized to the expression levels of mouse β-actin, β-tubulin, and EEF1A, according to the GeNorm method (Carmeliet and Jain, 2011). Error bars represent ±SD (2 experiments; each condition in triplicates); *$P<0.05$.

FIG. 22A, inhibition of Olfml3 expression in t.End.V1high cells after transfection of three Olfml3 siRNAs (Olfml3 siRNA 1, 2, and 3), compared with transfection using control siRNAs: siRNA non-homologous to any known mouse gene (ctrl siRNA) or GAPDH siRNA. At 24 hours after transfection, expression of target and reference genes were analyzed by RT-qPCR. The values were normalized to the expression levels of mouse β-actin, β-tubulin, and EEF1A, according to the GeNorm method (Carmeliet and Jain, 2011). Olfml3 siRNA 3 silenced >85% of the Olfml3 mRNA in t.End.V1high cells after transfection and was used for all subsequent experiments. Abbreviations: GAPDH, glyceraldehyde-3-phosphate dehydrogenase; siRNAs, small interfering RNAs; RT-qPCR, real-time quantitative polymerase chain reaction. Bars represent mean±SD (3 experiments, each condition in triplicates); *$P<0.05$; $P<0.01$; *$P<0.001$; ns—non significant. FIG. 22B, HEK293e cell suspension in serum-free media was used to produce rOlfml3 FLAG-tagged protein in the soluble form. The protein was affinity-purified on an anti-FLAG affinity column and eluted with FLAG peptides. Shown are Western blots of affinity-purified protein after immunoreactions with 1, anti-FLAG (M2) or 2, anti-Olfml3A+B antibody. A unique 54-kDa Olfml3 band appears in either condition.

FIGS. 24A-C. Structural domains of mouse Olfml3 protein and peptide sequences used for generation of anti-Olfml3 A+B and its immunoreactivity. FIG. 24A, peptide sequences used for generation of anti-Olfml3A+B: peptide A (red, 86-99 aa) comprises epitopes in the coiled-coil domain (orange, 25-101 aa) and peptide B (blue, 390-403 aa) comprises epitopes in the olfactomedin-like domain (green, 134-401 aa). FIG. 24B, Comparison of human and mouse Olfml3 protein sequences showed complete homology in the protein regions used for generation of anti-Olfml3 A+B. FIG. 24C, immunoreactivity of the rabbit anti-Olfml3A+B antibody (serum) against Olfml3 peptide A (left panel) and Olfml3 peptide B (right panel).

FIG. 25A, 9-day-old LLC1 tumors in mice treated with rat IgG$_{2B}$ (isotype control), 9F8BO (anti-Olfml3$^B$) or 46A9BO (anti-Olfml3$^B$) antibodies. Bar corresponds to 1 cm. FIG. 25B, reduced tumor weight in mice treated with 9F8BO (anti-Olfml3$^B$) or 46A9BO (anti-Olfml3$^B$) antibodies compared with control IgG$_{2B}$-treated tumors. Error bars represent ±SEM (1 experiment; 5 mice/group; 2 tumors/mouse). *$P<0.05$.

DESCRIPTION OF ILLUSTRATIVE EMBODIMENTS

Figures 1A, 1B:
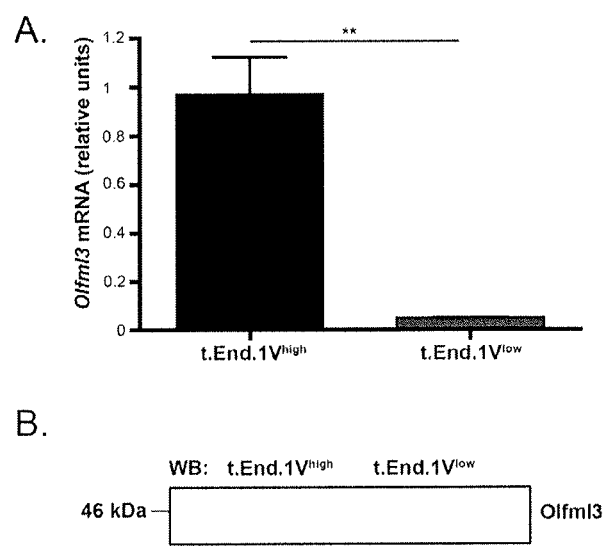
FIGS. 1A-1B. Differential expression of Olfml3 mRNA in angiogenic (t.End.1V$^{high}$) versus resting (t.End.1V$^{low}$) endothelial cells.

In clinical trials, beneficial effects of anti-angiogenic drugs were so far reached with antibodies against VEGF in the context of colon and breast carcinomas. However, it was less successful with other tumors for which alternate factors may be involved. Thus, other molecules involved in angiogenesis should be identified and used in combination with the growth factors. Specific targeting of vascular molecules expressed and/or secreted by angiogenic endothelial cells might be useful.

The present invention is based, in part, on the finding that Olfml3 exhibits proangiogenic function in tumors possibly mediated through the modulation of BMP4 signaling in vascular endothelial cells. Olfml3 is found to be a novel angiogenic regulator. To study its function in angiogenesis, Olfml3 is identified in the Examples as a binding partner of BMP4, a growth factor known for its proangiogenic activity in cancer progression. Binding of Olfml3 to BMP4 enhances BMP4 signaling to the Extracellular Signal-Regulated Kinase 1/2 (ERK1/2) cascade and stimulates endothelial cell proliferation, migration and sprouting. Thus, Olfml3 is an endothelial cell-derived proangiogenic factor and provides an alternative target for modulating tumor angiogenesis. Without wishing to be bound by theory, method are provided herein by targeting at least one of the Olfml3 domains that mediate the binding between Olfml3 protein and BMP4 protein. Further embodiments and advantages of the invention are described below.

I. Olfml3 Binding Molecules

In certain embodiments, an antibody or binding molecule that binds to at least a particular portion of Olfml3 protein and inhibits Olfml3 activity in angiogenesis and methods for treatment of diseases using such an antibody or binding molecule are contemplated. For example, the particular portion of Olfml3 targeted may be a part of one or more BMP4-binding domains on Olfml3. In a particular aspect, the particular portion may be an amino acid sequence defined by (i) amino acid positions 86-403, (ii) amino acid positions 86-99, (iii) amino acid positions 114-143, or (iv) amino acid positions 390-403 of SEQ ID NO:1 (human Olfml3) or SEQ ID NO:3 (mouse Olfml3). In a further aspect, the particular portion may be a functional variant that has an amino acid sequence at least 80%, 85%, 90%, 95%, 97%, 98%, 99% or 100% identical to the amino acid sequence defined as above.

This is the first report describing Olfml3 as a BMP4 agonist that promotes endothelial cell functions, at least in part, through the binding to BMP4 and stimulation of BMP4 signaling. Two mechanisms that interfere with BMP activation and signaling have been proposed. The first is the intracellular regulation of BMP cleavage into the secreted, active forms while the second involves binding of the extracellular BMPs to different BMP agonist/antagonist. Depending on the nature of BMP interacting molecules, BMP receptor binding activity may be activated or inhibited (Umulis et al., 2009). According to the data, the Olfml3-BMP4 interaction leads to an activated BMP4 complex. Olfml3 likely keeps the BMP4-receptor interactions and kinetics within a physiologically useful range. Olfml3 binds to BMP4 and possibly increases the affinity of BMP4 for its receptors, accounting for the activation of BMP4 signaling that the inventors observed in cultured endothelial cells. Indeed, when either BMP4 or Olfml3 is absent, induction of BMP4 signaling is suppressed. Another possibility is that Olfml3 may also promote BMP4 activity by dislodging the growth factor from a putative BMP antagonist in the extracellular space, as it was shown for pro-BMP activity of Twisted gastrulation (Twseg1) (Oelgeschlager et al., 2000). This mode of action is apparently different from the dose-dependent BMPER activity during regulation of BMP4 signaling in endothelial cells (Zhang et al., 2007; Serpe et al., 2008). At low molar concentration, BMPER presents BMP4 to its receptors and activates BMP4 signaling. At high molar concentrations, BMP4 binds preferentially to BMPER and it is not available for the receptor binding, hence inhibiting BMP4 signaling. Additional studies are needed to elucidate definitive Olfml3 mode of action to stabilize BMP4 and potentiate its signaling in endothelial cells.

Olfactomedin-like protein 3 (Olfml3) is a protein that in humans is encoded by the Olfml3 gene. The inventors used the t.End.1V$^{high}$ angiogenic and t.End.1V$^{low}$ resting cell lines to identify novel molecules differentially expressed and associated with angiogenesis. Among the identified new angiogenesis-associated genes, which fulfill the criteria described above they identified the mouse Olfml3 gene (olfactomedin-like 3).

The Olfactomedin-like 3 (Olfml3) gene encodes a secreted, extracellular protein, also known as ONT1 in *Xenopus* and chicken, mONT3 in mice, and HNOEL-iso or hOLF44 in humans (Zeng et al., 2004; Sakuragi et al., 2006; Inomata et al., 2008; Ikeya et al., 2005). Olfml3 belongs to a large family of olfactomedin domain-containing proteins with distinct roles in neurogenesis, neural crest formation, dorso-ventral patterning, cell cycle regulation, and tumorigenesis (reviewed in Tomarev et al., 2009). Together with Olfactomedin-like 1 (Olfml1), Olfml3 forms the Olfactomedin-like subfamily VII (Ikeya et al., 2005; Tomarev et al., 2009). Olfml3 is preferentially expressed in human placenta and secreted in the extracellular compartment, suggesting a possible Olfml3 function in the extracellular matrix-related processes during placental development (Zheng et al., 2004). This secreted protein contains a putative signal peptide and a coiled-coil domain at the N-terminus and Olfactomedin-like domain at the C-terminus.

The olfactomedin-like (ONT) subfamily is distinct from the olfactomedin (OLF) subfamily consisting of well-characterized members such as olfactomedin. The phylogenetic analysis revealed the olfactomedin-like domains are highly conserved among this subfamily of olfactomedin-like proteins with more than 90% homology in the mouse, rat and human counterparts of ONT3 (Olfml3) and at lesser extent (64%) in the chicken cONTI (Olfml3). However, the homology of the Olfactomedin-like domains to the Olfactomedin domains of noelin, tiarin or other olfactomedin family members is as low as 30% (Ikeya et al., 2005).

Bone morphogenetic protein 4 (BMP4) belongs to the BMP2/4 subgroup of the BMP family, sharing 92% homology with BMP2 (Celeste et al., 1990). BMP2 stimulates angiogenesis in developing tumors (Langenfeld and Langenfeld, 2004; Raida et al., 2005), through recruitment of endothelial progenitor cells and triggering tumor stromal cells to produce and secrete proangiogenic factors such as VEGF and PlGF (Raida et al., 2006). During embryonic development, BMP4 is critical for the induction of the mesoderm, endothelial progenitor cell differentiation and vasculogenesis (e.g. blood vessel formation) (Astorga and Carlsson, 2007; Winnier et al., 1995). Additionally, BMP4 regulates ocular angiogenesis through stimulation of VEGF secretion by retinal pigment epithelial cells (Valdimarsdottir et al., 2002; Vogt et al., 2006). Endothelial progenitor cells from human blood produce and secret both BMP2 and BMP4, which then promote neovascularization (Smadja et al., 2008). In mouse embryonic stem cells, proangiogenic effects of BMP4 are mediated through the activation of the VEGF/VEGF receptor 2 (VEGFR2), angiopoietin-1/Tie2 and Smad signaling pathways (Suzuki et al., 2008). The extracellular signal-regulated kinase 1/2 (ERK1/2) signaling pathway is shown to be a central regulator for BMP4 signal transduction, leading to capillary sprouting in human umbilical vein endothelial cells (HUVECs; Zhou et al., 2007). Additionally, BMP4 also acts as a chemo-attractant for endothelial cells migrating to the tumor and promotes tumor cell migration and invasion (Rothhammer et al., 2007).

The activities of BMPs are tightly regulated through a family of cysteine-knot proteins (Balemans and Van Hul, 2002; Rosen, 2006; Walsh et al., 2010). The reactivation of previously quiescent expression of BMP binding proteins can contribute to tumor progression. It has been reported that BMP binding proteins posses both anti- and pro-angiogenic activities during normal and pathological conditions (reviewed in (Moreno-Miralles et al., 2009).

In certain aspects, methods and compositions may be provided to inhibit the binding between Olfml3 and BMP4, for example, by molecules that specifically block the Olfml3 binding site for BMP4. Such molecules may be an antibody, a synthetic peptide or a small molecule. The antibody may be selected from the group consisting of a chimeric antibody, an affinity matured antibody, a polyclonal antibody, a monoclonal antibody or a humanized antibody, and a human antibody. In a particular example, the antibody is a monoclonal antibody or a humanized antibody. In another example, the antibody is a polyclonal antibody.

In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody of the invention has murine V regions and human C region. In one embodiment, the murine light chain V region is fused to a human kappa light chain. In one embodiment, the murine heavy chain V region is fused to a human IgG1 C region.

Examples of antibody fragments suitable for the present invention include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (US Patent App. Pub. 20050214860). Fv, scFv or diabody molecules may be stabilized by the incorporation of disulphide bridges linking the VH and VL domains. Minibodies comprising a scFv joined to a CH3 domain may also be made (Hu et al, 1996).

A polyclonal antibody for a particular domain of Olfml3 protein may be provided in certain aspects. Animals may be inoculated with an antigen, such as a particular portion of Olfml3 protein, in order to produce antibodies specific for the particular portion of Olfml3 protein. Such an antigen may be bound or conjugated to another molecule to enhance the immune response. As used herein, a conjugate is any peptide, polypeptide, protein or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. Hybridoma technology involves the fusion of a single B lymphocyte from a mouse previously immunized with an Olfml3 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced. However, in therapeutic applications a goal of hybridoma technology is to reduce the immune reaction in humans that may result from administration of monoclonal antibodies generated by the non-human (e.g. mouse) hybridoma cell line.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules which retain the antigen or epitope specificity of the original antibody, i.e., the molecule has a binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513, and 6,881,557, which are incorporated herein by this reference.

By known means as described herein, polyclonal or monoclonal antibodies, antibody fragments and binding domains and CDRs (including engineered forms of any of the foregoing), may be created that are specific to Olfml3 protein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by this reference. These techniques are further described in: Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art and highly predictable. Methods for producing these antibodies are also well known and predictable. For example, the following U.S. patents and patent applications provide enabling descriptions of such methods and are herein incorporated by reference: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

It is fully expected that antibodies to particular domains of Olfml3 will have the ability to neutralize or counteract the effects of the Olfml3, possibly through the binding to BMP4, regardless of the animal species, monoclonal cell line or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response and, thus, antibodies without Fc may be preferential for prophylactic or therapeutic treatments. As described above, antibodies may also be constructed so as to be chimeric, partially or fully human, so as to reduce or eliminate the adverse immunological consequences resulting from administering to an animal an antibody that has been produced in, or has sequences from, other species.

II. Lipid Preparations

In certain aspects, the present invention provides methods and compositions for associating an inhibitory antibody with a lipid and/or liposome. The inhibitory antibody may be encapsulated in the aqueous interior of a liposome, interspersed within the lipid bilayer of a liposome, attached to a liposome via a linking molecule that is associated with both the liposome and the polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The liposome or liposome/antibody associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine (DOPC).

"Liposome" is a generic term encompassing a variety of unilamellar, multilamellar, and multivesicular lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, certain aspects of the present invention also encompass compositions that have different structures in solution than the normal vesicular structure. For example, the lipids may assume a micellar structure or merely exist as non-uniform aggregates of lipid molecules. Also contemplated are lipofectamine-nucleic acid complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer of a polynucleotide in vitro and in vivo, then they are applicable for the present invention.

Exemplary lipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, dilinoleoylphosphatidylcholine, phosphatidylcholines, phosphatidylglycerols, phosphatidylethanolamines, cholesterol.

Liposomes and lipid compositions in certain aspects of the present invention can be made by different methods. The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Lipids suitable for use according to the present invention can be obtained from commercial sources. For example, dimyristyl phosphatidylcholine ("DMPC") can be obtained from Sigma Chemical Co., dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol.

Liposomes within the scope of the present invention can be prepared in accordance with known laboratory techniques. In certain embodiments, liposomes are prepared by mixing liposomal lipids, in a solvent in a container (e.g., a glass, pear-shaped flask). The container will typically have a volume ten-times greater than the volume of the expected suspension of liposomes. Using a rotary evaporator, the solvent may be removed at approximately 40° C. under negative pressure. The solvent may be removed within about 5 minutes to 2 hours, depending on the desired volume of the liposomes. The composition can be dried further in a desiccator under vacuum. Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

Liposomes can also be prepared in accordance with other known laboratory procedures: the method of Bangham et al. (1965), the contents of which are incorporated herein by reference; the method of Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

Dried lipids or lyophilized liposomes may be dehydrated and reconstituted in a solution of inhibitory peptide and diluted to an appropriate concentration with a suitable solvent (e.g., DPBS). The mixture may then be vigorously shaken in a vortex mixer. Unencapsulated nucleic acid may be removed by centrifugation at 29,000 g and the liposomal pellets washed. The washed liposomes may be resuspended at an appropriate total phospholipid concentration (e.g., about 50-200 mM). The amount of nucleic acid or antibody encapsulated can be determined in accordance with standard methods. After determination of the amount of nucleic acid or antibody encapsulated in the liposome preparation, the liposomes may be diluted to appropriate concentrations and stored at 4° C. until use.

III. Treatment of Diseases

Certain aspects of the present invention can be used to prevent or treat a disease or disorder associated with Olfml3 mediated angiogenesis. Functioning of Olfml3 may be reduced or enhanced by any suitable drugs to stimulate or prevent angiogenesis. Such exemplary substances can be an anti-Olfml3 antibody or a nucleic acid encoding such an antibody, particularly an antibody recognizes and binds to specific domains of Olfml3, soluble Olfml3 receptors or blocking small molecules.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a nucleic acid that inhibits the expression of a gene that encodes a Olfml3 and a lipid for the purposes of minimizing the growth or invasion of a tumor, such as a colorectal cancer.

A "subject" refers to either a human or non-human, such as primates, mammals, and vertebrates. In particular embodiments, the subject is a human.

The term "therapeutic benefit" or "therapeutically effective" as used throughout this application refers to anything that promotes or enhances the well being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

Certain aspects of the present invention may be used to treat any condition or disease associated with increased or decreased expression of Olfml3. For example, the disease may be an angiogenesis-related condition or disease. Angiogenesis-related condition or disease is a consequence of an imbalanced angiogenic process resulting in an excessive amount of new blood vessels or insufficient number of blood vessels.

In certain embodiments, the present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis, e.g., for controlling weight or promoting fat loss, for reducing cholesterol levels, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy, age-related macular degeneration (ARMD), psoriasis, rheumatoid arthritis and other inflammatory diseases. These diseases are characterized by the destruction of normal tissue by newly formed blood vessels in the area of neovascularization. For example, in ARMD, the choroid is invaded and destroyed by capillaries. The angiogenesis-driven destruction of the choroid in ARMD eventually leads to partial or full blindness. The angiogenesis-related conditions also include ocular neovascularization, arterio-venous malformations, coronary restenosis, peripheral vessel restenosis, glomerulonephritis, rheumatoid arthritis, ischemic cardiovascular pathologies, or chronic inflammatory diseases.

Exemplary eye angiogenic diseases to be treated or prevented also include choroidal neovascularization (CNV) due to any cause including but not limited to age-related macular degeneration, ocular histoplasmosis, pathologic myopia, and angioid streaks. It also applies to retinal neovascularization of any cause including but not limited to proliferative diabetic retinopathy, retinal vein occlusions, and retinopathy of prematurity. It also applies to iris neovascularization and corneal neovascularization of any causes.

The neovascularization may also be neovascularization associated with an ocular wound. For example, the wound may be the result of a traumatic injury to the globe, such as a corneal laceration. Alternatively, the wound may be the result of ophthalmic surgery. In some embodiments, the methods of the present invention may be applied to prevent or reduce the risk of proliferative vitreoretinopathy following vitreoretinal surgery, prevent corneal haze following corneal surgery (such as corneal transplantation and laser surgery), prevent closure of a trabeculectomy, prevent or substantially slow the recurrence of pterygii, and so forth.

The neovascularization may be located either on or within the eye of the subject. For example, the neovascularization may be corneal neovascularization (either located on the corneal epithelium or on the endothelial surface of the cornea), iris neovascularization, neovascularization within the vitreous cavity, retinal neovasculization, or choroidal neovascularization. The neovascularization may also be neovascularization associated with conjunctival disease.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Nonetheless, it is also recognized that certain aspects of the present invention may also be used to treat a non-cancerous disease (e.g., a fungal infection, a bacterial infection, a viral infection, and/or a neurodegenerative disease).

In certain embodiments, Olfml3 protein or peptide is contemplated to treat angiogenesis-related conditions in a subject in need of angiogenesis. Insufficient angiogenesis is related to a large number of diseases and conditions, such as cardiovascular diseases, transplantation, aneurisms and delayed wound healing. Therapeutic angiogenesis is aimed at stimulating new blood vessel growth. The concept of such a therapy is based on the premise that the inherent potential of vascularization in a vascular tissue can be utilized to promote the development of new blood vessels under the influence of the appropriate angiogenic molecules.

In certain aspect, the Olfml3 antibodies may be used to reduce pericytes, particularly in vessels associated with tumor or tumor vessels. Pericytes are critical regulators of vascular morphogenesis and function. Shortly after endothelial tubes form, they become associated with mural cells. These cells provide structural support to the vessels and are important regulators of blood flow. Pericytes constitute a heterogeneous population of cells. Several functions of pericytes during angiogenesis have been proposed, including sensing the presence of angiogenic stimuli, depositing or degrading extracellular matrix and controlling endothelial cell proliferation and differentiation in a paracrine fashion. In certain diseases such as diabetic retinopathy, pericytes may be the primary affected vascular cells, which lead to secondary effects on the endothelial cells.

IV. Pharmaceutical Preparations

Where clinical application of a composition containing an inhibitory antibody is undertaken, it will generally be beneficial to prepare a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The phrases "pharmaceutical or pharmacologically acceptable" refer to molecular entities and compositions that do not produce an adverse, allergic or other untoward reaction when administered to an animal, such as a human, as appropriate. The preparation of a pharmaceutical composition comprising a inhibitory antibody or additional active ingredient will be known to those of skill in the art in light of the present disclosure, as exemplified by Remington (2005), incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is particularly formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 microgram/kg/body weight to about 500 milligram/kg/body weight, etc., can be administered.

A gene expression inhibitor may be administered in a dose of 1-100 (this such range includes intervening doses) or more µg or any number in between the foregoing of nucleic acid per dose. Each dose may be in a volume of 1, 10, 50, 100, 200, 500, 1000 or more µl or ml or any number in between the foregoing.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

In particular embodiments, the compositions of the present invention are suitable for application to mammalian eyes. For example, the formulation may be a solution, a suspension, or a gel. In some embodiments, the composition is administered via a biodegradable implant, such as an intravitreal implant or an ocular insert, such as an ocular insert designed for placement against a conjunctival surface. In some embodiments, the therapeutic agent coats a medical device or implantable device.

In preferred aspects the formulation of the invention will be applied to the eye in aqueous solution in the form of drops. These drops may be delivered from a single dose ampoule which may preferably be sterile and thus rendering bacteriostatic components of the formulation unnecessary. Alternatively, the drops may be delivered from a multi-dose bottle which may preferably comprise a device which extracts preservative from the formulation as it is delivered, such devices being known in the art.

In other aspects, components of the invention may be delivered to the eye as a concentrated gel or similar vehicle which forms dissolvable inserts that are placed beneath the eyelids.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, or respiratory tract, aerosol delivery can be used. Volume of the aerosol is between about 0.01 ml and 0.5 ml.

An effective amount of the therapeutic composition is determined based on the intended goal. For example, one skilled in the art can readily determine an effective amount of the antibody of the invention to be administered to a given subject, by taking into account factors such as the size and weight of the subject; the extent of the neovascularization or disease penetration; the age, health and sex of the subject; the route of administration; and whether the administration is regional or sysemic. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

V. Combination Treatments

In certain embodiments, the compositions and methods of the present invention involve an inhibitor of expression of Olfml3, or construct capable of expressing an inhibitor of Olfml3 expression, or an antibody or an antibody fragment against Olfml3 to inhibit its activity in angiogenesis, in combination with a second or additional therapy. Such therapy can be applied in the treatment of any disease that is associated with increased expression or activity of Olfml3. For example, the disease may be an angiogenesis-related disease.

The methods and compositions including combination therapies enhance the therapeutic or protective effect, and/or increase the therapeutic effect of another anti-angiogenesis, anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an inhibitor of gene expression and a second therapy. A tissue, tumor, or cell can be contacted with one or more compositions or pharmacological formulation(s) including one or more of the agents (i.e., inhibitor of gene expression or an anti-cancer agent), or by contacting the tissue, tumor, and/or cell with two or more distinct compositions or formulations, wherein one composition provides 1) an inhibitor of gene expression; 2) an anti-cancer agent, or 3) both an inhibitor of gene expression and an anti-cancer agent. Also, it is contemplated that such a combination therapy can be used in conjunction with a chemotherapy, radiotherapy, surgical therapy, or immunotherapy.

An inhibitor of gene expression and/or activity may be administered before, during, after or in various combinations relative to an anti-cancer treatment. The administrations may be in intervals ranging from concurrently to minutes to days to weeks. In embodiments where the inhibitor of gene expression is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the inhibitor of gene expression therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1-90 days, or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc.

Various combinations may be employed. For the example below an inhibitor of gene expression therapy is "A" and an anti-cancer therapy is "B":

A/B/AB/A/BB/B/AA/A/BA/B/BB/A/AA/B/B/BB/A/B/B
B/B/B/A B/B/A/B A/A/B/B A/B/A/BA/B/B/AB/B/A/A
B/A/B/A B/A/A/B A/A/A/BB/A/A/AA/B/A/AA/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a standard therapy will include antiangiogenic therapy, chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

A. Antiangiogenic Therapy

The skilled artisan will understand that additional antiangiogenic therapies may be used in combination or in conjunction with methods of the invention. For example additional antiangiogenic therapies may antagonize the VEGF and/or FGF signaling pathway. Thus, in some cases and additional therapy may comprise administration an antibody that binds to VEGF, a VEGF receptor, FGF or an FGF receptor. In certain specific aspects, methods and compositions of the invention may be used in conjunction with AVASTIN® (bevacizumab), LUCENTIS® (ranibizumab), MACUGEN® (pegaptanib sodium) or an anti-inflammatory drug. Thus, in certain specific cases there is provided a therapeutic composition comprising an anti-Olfml3 composition and bevacizumab or pegaptanib sodium in a pharmaceutically acceptable carrier.

In still further aspects a gene that regulates angiogenesis may be delivered in conjunction with the methods of the invention. For example, in some aspects, a gene that regulates angiogenesis may be a tissue inhibitor of metalloproteinase, endostatin, angiostatin, endostatin XVIII, endostatin XV, kringle 1-5, PEX, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP10), a fusion protein of Mig and IP10, soluble FLT-1 (fms-like tyrosine kinase 1 receptor), and kinase insert domain receptor (KDR) gene. In certain specific aspects, such an angiogenic regulator gene may be delivered in a viral vector such as the lentiviral vectors described in U.S. Pat. No. 7,122,181, incorporated herein by reference.

B. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

C. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

D. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gene silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

E. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that certain aspects of the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with certain aspects of the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1 beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increase of intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with certain aspects of the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VI. Kits and Diagnostics

In various aspects of the invention, a kit is envisioned containing therapeutic agents and/or other therapeutic and delivery agents. In some embodiments, the present invention contemplates a kit for preparing and/or administering a therapy of the invention. The kit may comprise one or more sealed vials containing any of the pharmaceutical compositions of the present invention. In some embodiments, the lipid is in one vial, and the Olmlf3 inhibitory molecule component is in a separate vial. The kit may include, for example, at least one inhibitor of Olfml3 function, such as an Olfml3 domain-specific antibody, one or more lipid component, as well as reagents to prepare, formulate, and/or administer the components of the invention or perform one or more steps of the inventive methods. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of a therapeutic agent.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Differential Olfml3 Gene Expression in Angiogenic Versus Resting Endothelial Cells To mimic molecular and functional properties of endothelial cells during tumor angiogenesis, the inventors previously isolated two subpopulations of an endothelioma cell line with molecular characteristics of angiogenic (t.End.1V$^{high}$) and resting (t.End.1V$^{low}$) states (Aurrand-Lions et al., 2004). The t.End.1V$^{high}$ cells express high levels of the integrin αVβ3 and do not endocytose acetylated low-density lipoprotein (Ac-LDL), while t.End.1V$^{low}$ cells express low levels of αVβ3 integrin and efficiently take up Ac-LDL. In contrast, t.End.1V$^{high}$ cells show increased migration and form capillary-like structures in three dimensional (3D) fibrin gels (Aurrand-Lions et al., 2004). Therefore, t.End.1V$^{high}$ and t.End.1V$^{low}$ cells appeared to be suitable cellular representatives of angiogenic and resting endothelial cells. These cells were exploited as a starting point for the transcriptomic profiling using Affymetrix mouse 430 Gene Chip arrays. Data analysis resulted in more than 3500 differentially expressed genes with 1700 genes≥2-fold ($P≤0.05$) over-expressed in t.End.1V$^{high}$ cells (Miljkovic-Licina et al., 2009). To focus on novel genes that are relevant for angiogenesis, the microarray dataset was compared with a published dataset of genes upregulated after angiogenic activation of HUVEC by vMIP-II (viral macrophage inflammatory protein II) a chemokine with described proangiogenic activity (Cherqui et al., 2007). This comparison identified 38 genes, of which several were already implicated in the regulation of angiogenesis, validating the biological relevance of the experimental approach. The transcriptomic profiling further yielded several new candidate genes without known proangiogenic activity (Miljkovic-Licina et al., 2009). One of the most promising candidate genes in this category was Olfml3 (NM_133859), since its expression was remarkably upregulated in t.End.1V$^{high}$ cells (30 fold). Upregulation of Olfml3 gene expression was validated through quantitative real-time PCR analysis using total RNA isolated from angiogenic and resting cells (FIG. 1A) and Western blotting (FIG. 1B). Subsequent analysis focused on the characterization of Olfml3, as a novel differentially expressed angiogenic cell-derived factor.

Example 2

Expression of Olfml3 in Angiogenic Tissues

Figures 2A, 2B, 2C:
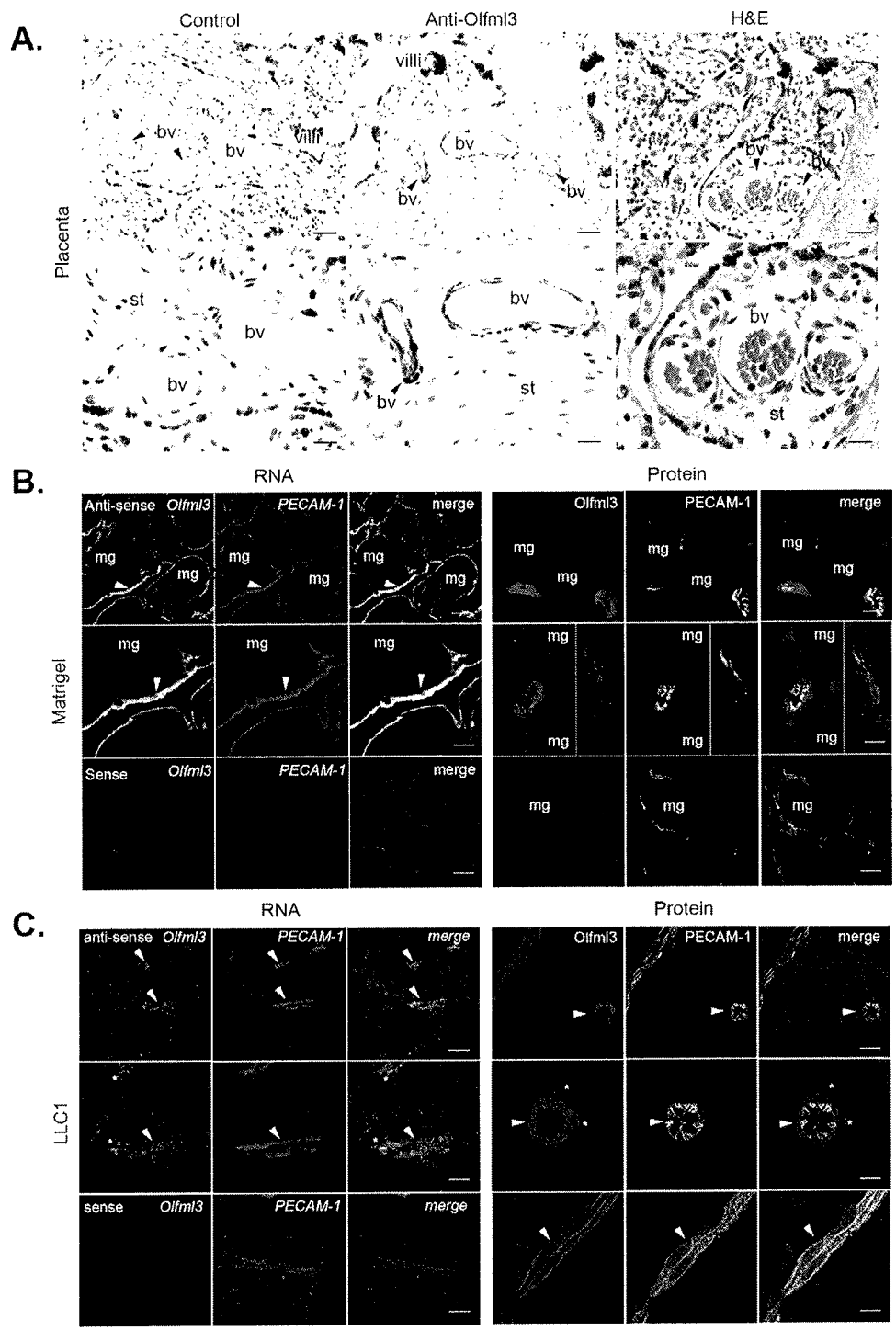
FIGS. 2A-2C. In vivo expression of Olfml3 in angiogenic tissues.
Figures 3A, 3B:
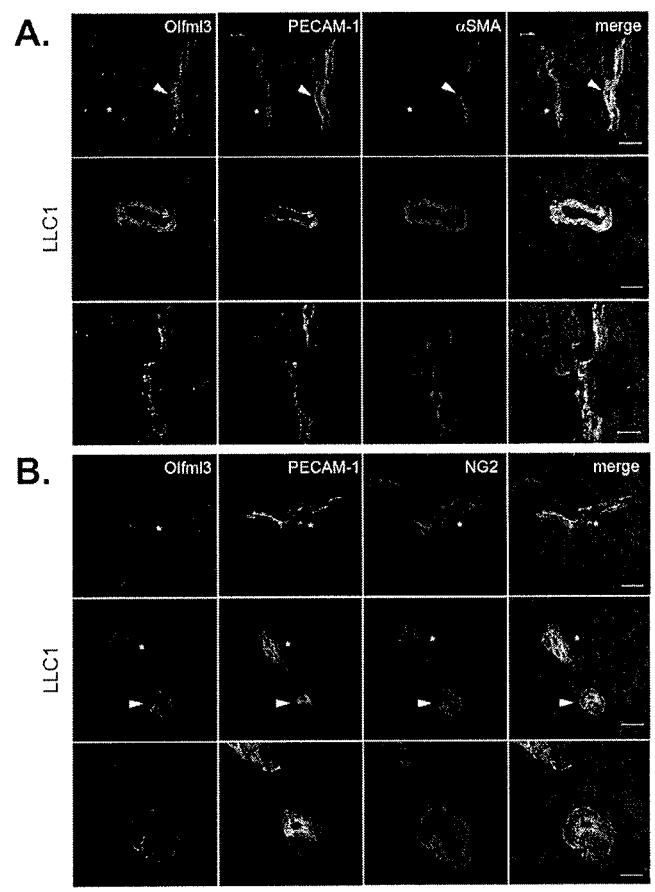
FIGS. 3A-3B. Olfml3 is secreted but remains in vicinity of endothelial cells associated with immature α-SMA-positive mural cells.

In mouse embryos, high levels of Olfml3 transcripts are detected during early embryogenesis in the presumptive vasculogenic regions (Ikeya et al., 2005; Drake and Fleming, 2000). In humans, the highest levels of Olfml3 transcripts are found in placenta but also in a few highly vascularized organs, such as heart and liver albeit at lower levels (Zheng et al., 2004). To determine localization of Olfml3 expression in these organs, the inventors analyzed the Olfml3 expression pattern using in situ mRNA hybridization or immunostaining. Interestingly, Olfml3 expression was strongly upregulated in capillaries and large vessels of human placenta, which is a tissue characterized by continuous angiogenesis (Khankin et al., 2010) (FIG. 2A). This unique expression pattern suggested that high levels of Olfml3 expression in placental vasculature might be associated with vascular growth and remodeling. Therefore, the inventors induced de novo formation of blood vessels in wild-type mice by subcutaneous injection of bFGF-loaded matrigel. After eight days, the vascularized plugs were harvested and in situ mRNA hybridization or immunostaining were performed on frozen samples. Double labeling using antisense RNA probes for Olfml3 and the endothelial marker PECAM-1 revealed robust endothelial specific expression of Olfml3 in these angiogenic blood vessels (FIG. 2B, left panel). Subsequently, the inventors were able to detect Olfml3 expression in angiogenic tumor vessels using subcutaneous Lewis Lung Carcinoma (LLC1) grafts in wt mice (FIG. 2C, left panel). These results were expanded by Olfml3 protein detection using double immunostaining for Olfml3 and platelet/endothelial cell adhesion molecule-1 (PECAM-1) in the bFGF-loaded matrigel plugs or in the LLC1 tumor tissue (FIGS. 2B-2C, right panels). Of interest, Olfml3 protein was enriched along the vessel wall of an angiogenic tumor vessel subset (FIG. 2C, right panel). To further characterize perivascular Olfml3 expression, the LLC1 tumors were triple stained using specific antibodies for Olfml3, PECAM-1 and the mural cell markers, α-smooth muscle actin (α-SMA) or NG2 chondroitin sulfate proteoglycan. Immunofluorescence microscopy revealed that Olfml3 expression was not only found on PECAM-1-positive endothelial cells but also overlapped with α-SMA-positive mural cells (FIG. 3A) and to a lesser extent, with NG2-positive pericytes (FIG. 3C). These observations indicate that expression of Olfml3 by tumor vessel-associated mural cells cannot be excluded, despite the fact that these cells were not shown to be positive for Olfml3 transcripts (FIGS. 2B-2C, left panels). The Olfml3-expressing tumor vessels were predominantly covered by α-SMA-positive mural cells (FIG. 3A), while none or partial overlapping of the Olfml3-expressing vessels was observed with NG2-positive pericytes (FIG. 3B). Intense α-SMA staining along with the reduced NG2 expression in the tumor-associated pericytes generally reflects a phenotype of more immature, highly angiogenic tumor blood vessels (Morikawa et al., 2002; Gerhardt et al., 2003). Therefore, these data suggest that Olfml3 expression and secretion are mainly associated with immature, highly angiogenic tumor vessels.

Example 3

Olfml3 is Required for Endothelial Cell Migration

Figures 4A, 4B, 4C, 4D, 4E:
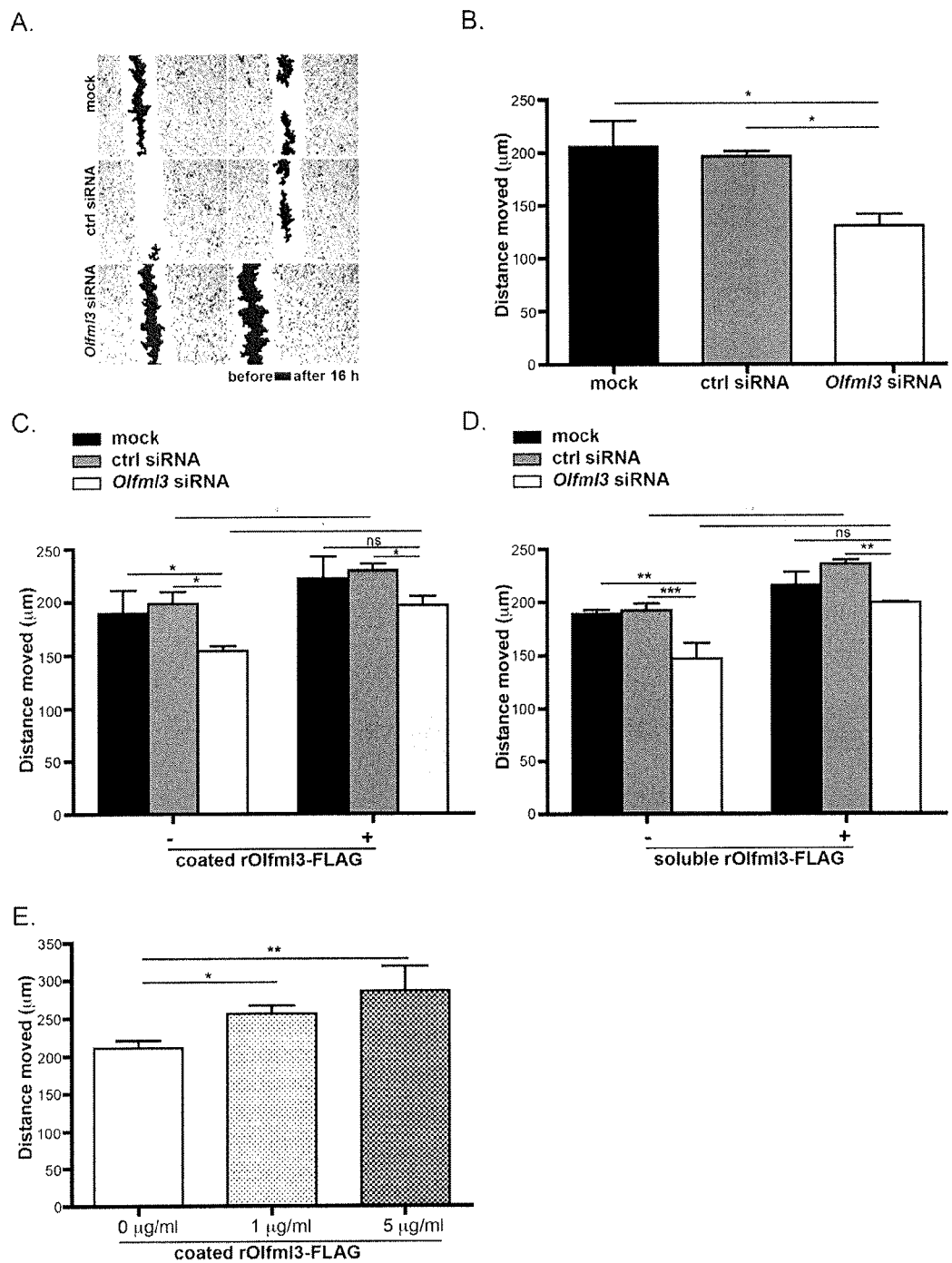
FIGS. 4A-4E. Delayed wound healing of Olfml3-silenced t.End.1V$^{high}$ cells.
Figure 9:
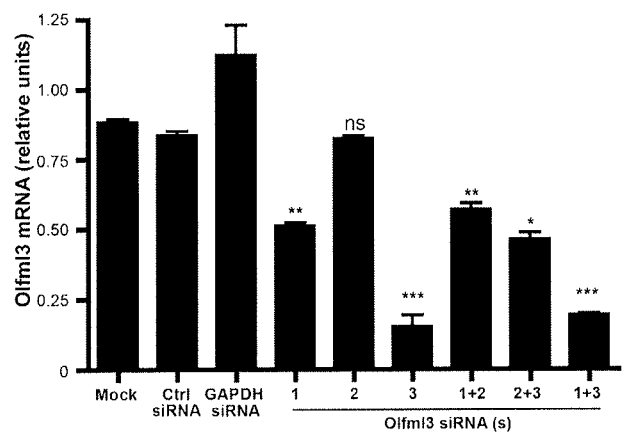
FIG. 9. Validation of Olfml3 down-regulation using siRNAs. Inhibition of Olfml3 expression in t.End.V1$^{high}$ cells using three siRNA sequences (Olfml3 siRNA 1, 2 and 3). Transfection of Olfml3-targeted and control (ctrl siRNA and GAPDH) siRNAs at the concentration of 0.5 μM was carried out using Nucleofector technology (Amaxa). At 24 hours post-transfection, expression of target and control genes were analyzed by qPCR. The values were normalized to the expression levels of mouse β-actin, β-tubulin and EEF1A. Abbreviations: nh siRNA, non homologous siRNA; GAPDH, glyceraldehyde-3-phosphate dehydrogenase; siRNAs, small interfering RNAs; qPCR, quantitative polymerase chain reaction.

To characterize the functions of Olfml3 in the extracellular compartment surrounding angiogenic cells, the inventors first tested whether Olfml3 mediates endothelial cell migration, an essential step of angiogenesis. As the t.End.1V$^{high}$ cells can migrate efficiently in wound healing assays (Aurrand-Lions et al., 2004), the inventors silenced Olfml3 expression in these cells and tested their migratory capacities in this assay. Three siRNAs were designed, of which siRNA 3 silenced >90% of the Olfml3 message in t.End.1V$^{high}$ cells (FIG. 9). As for controls, the inventors used mock-transfected t.End.1V$^{high}$ cells as well as cells transfected with either GAPDH siRNA or a control siRNA non-homologous to any known mouse genes (ctrl siRNA) (FIG. 9). The t.End.1V$^{high}$ cells transfected with siRNA 3 displayed a significantly decreased migration in wound healing assays in which the rate of cell migration into a denuded area was monitored (FIGS. 4A-4B). Mock or control siRNA transfection had no effect on t.End.1V$^{high}$ cell migration. Furthermore, reduced migratory ability of silenced t.End.1V$^{high}$ cells was partly compensated by coating or adding recombinant Olfml3 protein in vitro (FIGS. 4C-4D). In addition, when coated on culture plates, recombinant Olfml3 protein promoted t.End.1V$^{high}$ cell migration in a concentration-dependent manner (FIG. 4E). These data suggest that Olfml3 promotes migration of endothelial cells, a prerequisite for angiogenesis.

Example 4

Olfml3 is Required for Endothelial Sprouting In Vitro

Figure 5A:
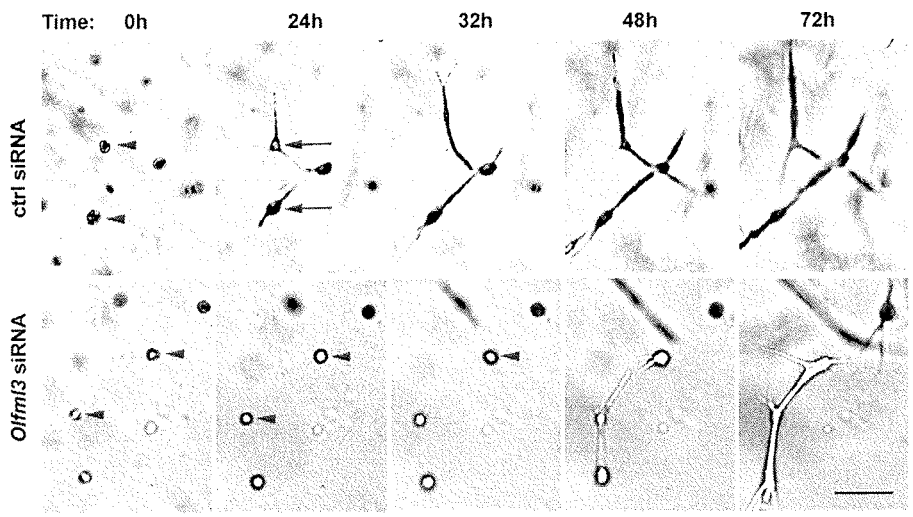
FIGS. 5A-5C. Silencing of Olfml3 in t.End.1V$^{high}$ cells attenuates the initiation and the final steps angiogenesis in vitro.
Figure 5B:
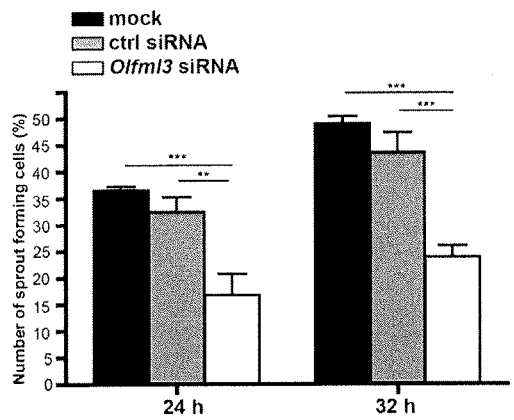
Figure 5C:
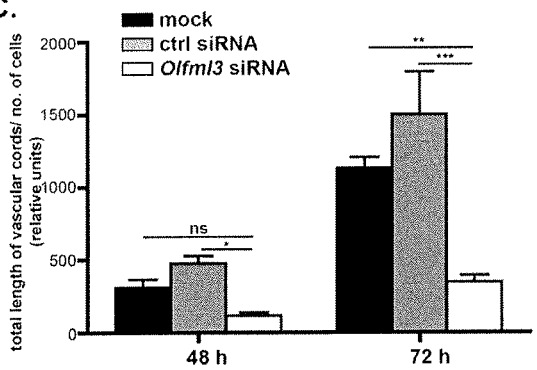
Figure 11:
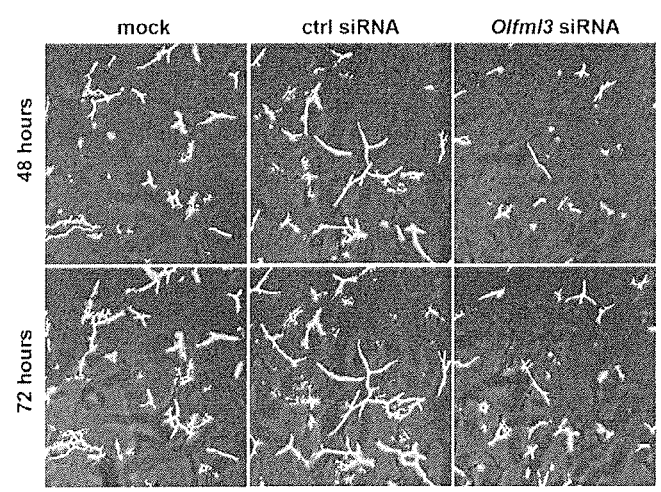
FIG. 11. Total length of vascular cords representing the capillary-like network quantified using MetaMorph software. Length and complexity of the vascular network (cords) of Olfml3-silenced cells (bottom panel) is reduced compared with control siRNA-transfected cells (top panel) at both 56 and 72 h.

Because the inventors observed Olfml3 involvement in endothelial cell migration, the inventors next examined whether Olfml3 is required for sprouting of endothelial cells, a subsequent step of angiogenesis. As the t.End.1V$^{high}$ cells efficiently form a capillary-like network of ramified cords in 3D fibrin gels (Aurrand-Lions et al., 2004; Pepper et al., 1996), the inventors used these cells to perform the endothelial sprout formation assay in vitro (FIGS. 5A-5C). In this assay, endothelial cells sprout in 3D fibrin gels and organize into structures morphologically similar to capillaries (Montesano et al., 1990; Pepper et al., 1996). Sprout formation starts with individual endothelial cells sending out filopodia-like protrusions (spikes) within 24 hours after cell seeding (FIG. 5A, 24 h panels). These spikes then initiate contacts with other cells in the vicinity, align and start forming capillary-like structures (FIG. 5A, 32-72 h panels). Using Olfml3-silenced t.End.1V$^{high}$ cells, the inventors observed a severe reduction of the number of spike-forming cells during the first 24-32 h (FIG. 5B) compared to mock or control siRNA-treated cells. At later time points (between 56-72 h), the inventors observed reduced a total length of the vascular network in the 0 μm/3-silenced cells when compared with the mock-transfected or control cells (FIG. 5C and FIG. 11). These results suggest that abrogation of Olfml3 delays endothelial sprout formation further demonstrating its key role in angiogenesis.

Example 5

Anti-Olfml3 Antibodies Reduce Tumor Growth In Vivo

Figure 13:
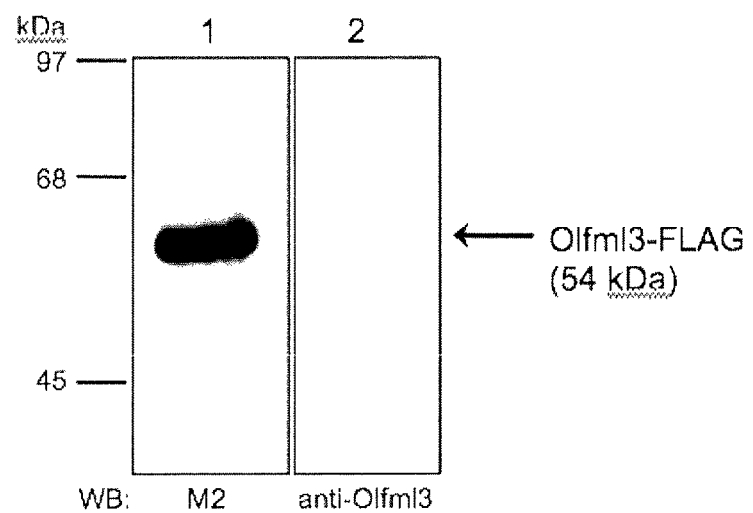
FIG. 13. HEK293e cells suspension in the serum-free media was used to produce Olfml3 FLAG-tagged protein in the soluble form. The protein was affinity purified on an anti-FLAG affinity column and eluted with FLAG peptide. Shown are Western blotting of affinity-purified protein after immunoreactions with anti-FLAG (M2) or anti-Olfml3 antibodies. A unique 54 kDa Olfml3 band appears in either condition.

The highly abundant Olfml3 expression in angiogenic tumor vessels (FIGS. 2A-2C, FIGS. 3A-3B) and its ability to promote endothelial migration and sprouting in vitro (FIGS. 4A-4E, FIGS. 5A-5C) prompted us to test whether Olfml3 is able to promote tumor angiogenesis in vivo. To test this hypothesis and to determine which structural domain of Olfml3 is necessary for its potential proangiogenic effect, the inventors generated rabbit anti-Olfml3 antibodies specific for two 13 amino acid long peptides comprising epitopes in the coiled-coil or the Olfactomedin-like domain of murine Olfml3 (peptide A or B respectively) (FIG. 12A). The sequence comparison of Olfml3 peptides used to generate these antibodies revealed no homology with the other members of the Olfactomedin protein family (data not shown), while both peptides were identical to the human Olfml3 protein sequence (FIG. 12B). The rabbit anti-Olfml3 antisera recognized specifically the Olfml3 peptides A and B (FIG. 12C) as well as mouse recombinant Olfml3 protein (FIG. 13).

Figures 6A, 6B, 6C, 6D, 6E, 6F:
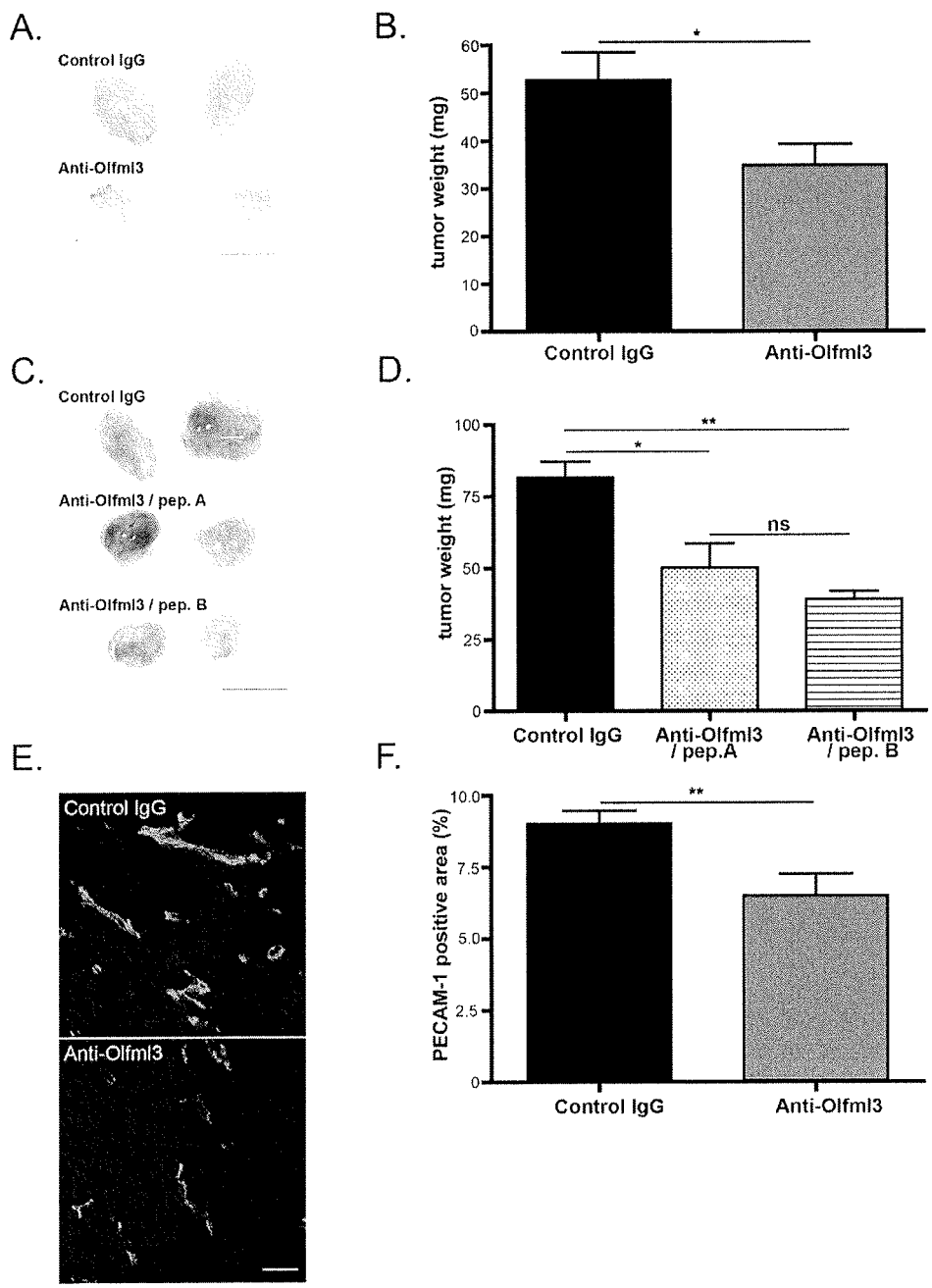
FIGS. 6A-6F. Treatment of mice with the anti-Olfml3 antibodies reduces tumor growth. C57BL6/J mice were injected subcutaneously (s.c.) with Lewis lung carcinoma cells (LLC1) into the flank. Mice received intraperitoneal (i.p.) injections of either control total rabbit IgG (ctrl IgG), or affinity-purified anti-Olfml3 every third day (50 µg).
Figure 10:
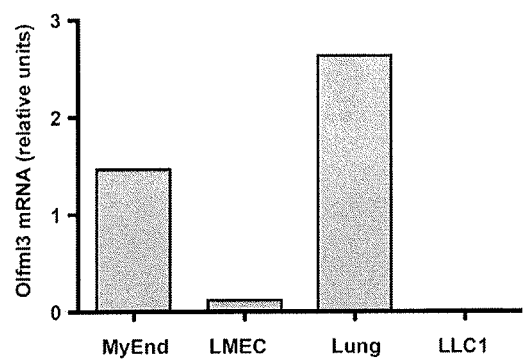
FIG. 10. Detection of Olfml3 mRNA in mouse MyEnd microvascular myocardial endothelial cells, LMEC primary lung microvascular endothelial cells, lung tissue and LLC1 Lewis lung carcinoma cells. Expression of Olfml3 and control genes were analyzed by qPCR. The values were normalized to the expression levels of mouse β-actin, β-tubulin, and EEF1A.

The anti-Olfml3 antibodies were first affinity-purified against both Olfml3 peptides and subsequently used for in vivo treatment of mice bearing LLC1 tumors. Tumor cells were injected subcutaneously and the anti-Olfml3 antibodies were given i.p. every 72 hours. At day 9, animals were sacrificed and the tumors excised. The anti-Olfml3 antibody treatments significantly decreased the tumor weight when compared to control rabbit IgG treated tumors (FIGS. 6A-6B). In order to determine which Olfml3 structural domain might be necessary for this effect, the inventors affinity-purified the anti-Olfml3 antibodies against either the Olfml3 peptide A or peptide B and used them for the LLC1 tumor treatment. Both antibodies significantly reduced tumor growth with no significant difference observed between either target (FIGS. 6C-6D). Because LLC1 tumor cells do not express Olfml3 (FIG. 2C and FIG. 10.), the reduction in tumor growth after anti-Olfml3 treatment was likely due to reduced angiogenesis. Indeed, the rate of the tumor vascularization measured by staining of the endothelial PECAM-1, was significantly decreased (26%) in the anti-Olfml3 treated tumors compared to the control antibody-treated tumors (FIGS. 6E-6F). This observation confirms the hypothesis that Olfml3 promotes tumor angiogenesis.

Example 6

Molecular Mechanism of Olfml3-Mediated Angiogenesis

Figure 7A:
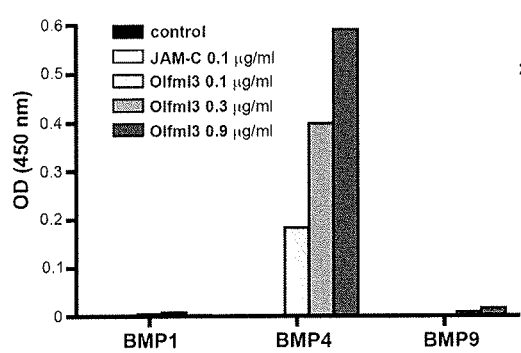
FIGS. 7A-7D. Recombinant Olfml3 binds recombinant BMP4.
Figure 7B:
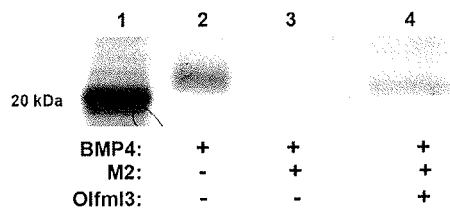
Figure 7C:
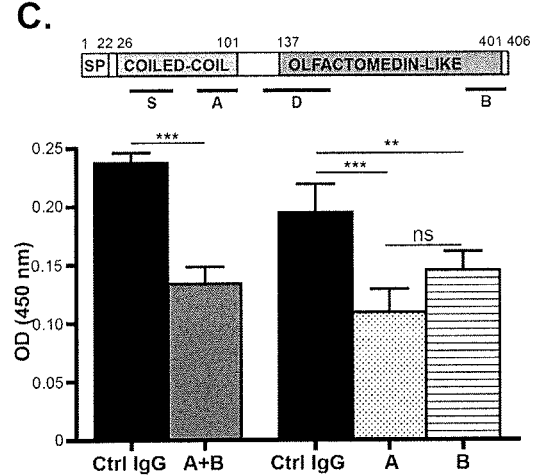
Figure 7D:
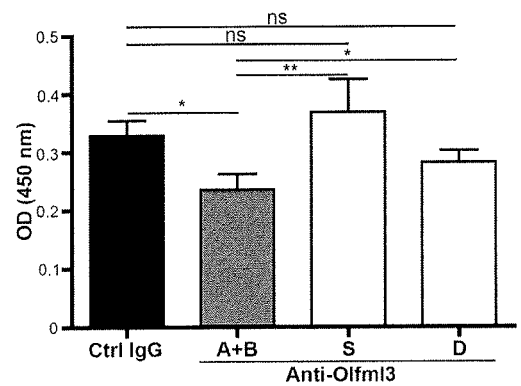

Previous studies have shown that ONT1, a *Xenopus* homologue of Olfml3, interacts with the BMP1/Tolloid-class proteinases and Chordin, a BMP antagonist, through the coiled-coil and the olfactomedin-like domain, respectively (Inomata, 2008). The inventors sought to investigate possible Olfml3 interactions with other BMP family members, particularly those with prominent proangiogenic activity in tumors such as BMP4. The inventors produced recombinant Olfml3 FLAG-tagged protein (rOlfml3-FLAG), purified from the total cell lysates and analyzed its expression by Western blotting, using anti-FLAG and anti-Olfml3 antibodies (FIG. 13). The rOlfml3-FLAG was then used for interaction studies using different BMPs using ELISA assays. The inventors found that rOlfml3-FLAG specifically binds recombinant BMP4 but not rBMP1 or rBMP9 (FIG. 7A) and confirmed that rOlfml3-FLAG co-immunoprecipitates with mouse recombinant BMP4 (FIG. 7B). Mass spectrometry analysis confirmed the identity of BMP4, as a binding partner of Olfml3 protein (FIG. 14). To map the BMP4-binding regions on the Olfml3 protein, four different anti-Olfml3 antibodies raised against non-overlapping Olfml3 peptide sequences, were used for the interaction studies (FIGS. 7C-7D). Three of the antibodies blocked Olfml3-BMP4 interaction and defined two binding domains on the Olfml3 protein, corresponding to the coiled-coil (Olfml3 peptide A) and the Olfactomedin-like domain (Olfml3 peptide B and D) (FIGS. 7C-7D). Therefore, the inventors demonstrate that both Olfml3 protein domains are equally required for the interaction with recombinant BMP4 protein. In contrast, *Xenopus* ONT1 binds BMP1 exclusively through the coiled-coil domain and it does not bind to BMP4 (Inomata et al., 2008). The results define a novel interaction between mouse Olfml3 and BMP4, a potent proangiogenic growth factor. The question arises whether the Olfml3-BMP4 interaction complex is needed to potentiate the proangiogenic effect of BMP4.

Example 7

Olfml3-BMP4 Interaction Promotes BMP4 Signaling in Endothelial Cells

Figure 8A:
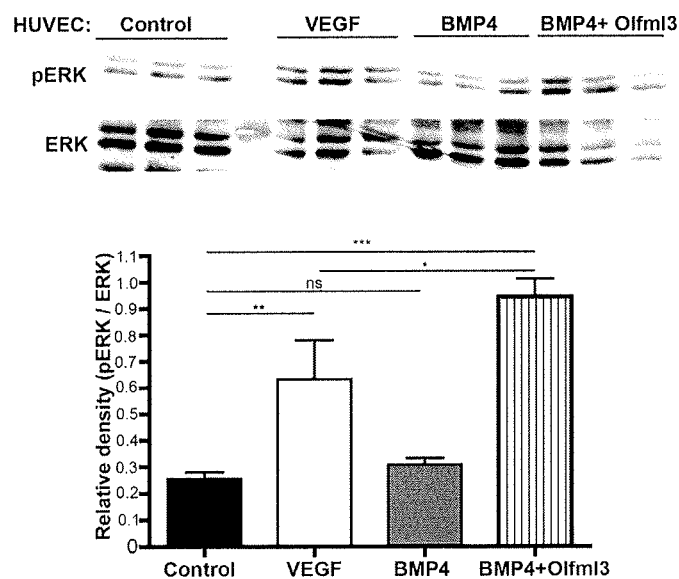
FIGS. 8A-8B. Olfml3-BMP4 interaction stimulates ERK1/2 phosphorylation.

BMP4 mediates a cellular response in endothelium through the activation of the ERK1/2 signaling pathway, thus regulating critical endothelial functions such as proliferation or tube formation in HUVECs (Langenfeld and Langenfeld, 2004; Zhou et al., 2007). Since the inventors demonstrated that BMP4 directly interacts with Olfml3 (FIGS. 7A-7D), the inventors sought to investigate the possible effect of this interaction in the induction of the ERK1/2 signaling in HUVECs. The level of the ERK1/2 phosphorylation in HUVECs treated with BMP4 in combination with Olfml3 was 5 fold increased compared to phosphorylation of untreated cells or those stimulated with BMP4 or Olfml3 individually (FIG. 8A). Moreover, the synergistic effect of BMP4 and Olfml3 on the ERK1/2 phosphorylation was higher than that following VEGF stimulation (FIG. 8A). This demonstrates that Olfml3 may act as an enhancer of BMP4-ERK1/2 signaling in HUVECs, suggesting that Olfml3-associated angiogenesis may occur, at least in part, through the activation of endothelial cells via this particular signaling cascade.

Figure 8B:
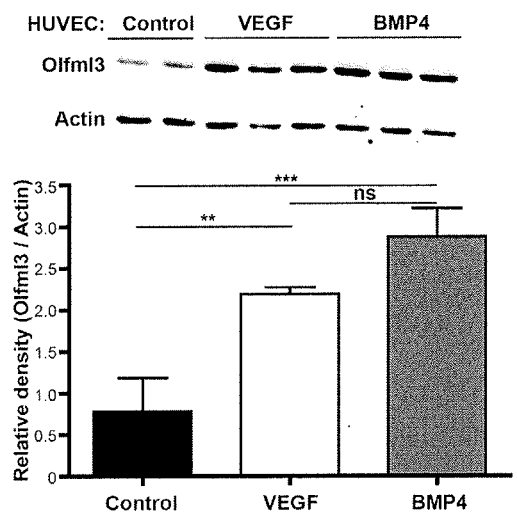

BMP4 induced activation of ERK1/2 signaling leads to increased BMP4 gene expression forming an autocrine feedback loop (Zhou et al., 2007). To check if Olfml3 gene expression is also under the BMP4 control, HUVECs were stimulated with BMP4 during 24 h, and upregulation of Olfml3 protein expression was detected after this period (FIG. 8B). Notably, BMP4-induced expression of Olfml3 was equally upregulated as Olfml3 expression induced by VEGF stimulation of HUVECs. These data suggest that Olfml3 expression is driven by angiogenic growth factors and it amplifies effects these factors have on endothelial cells.

Example 8

Dual Expression of Olfml3 in Tumor Endothelium and Accompanying Pericytes

Figures 15A, 15B, 15C, 15D:
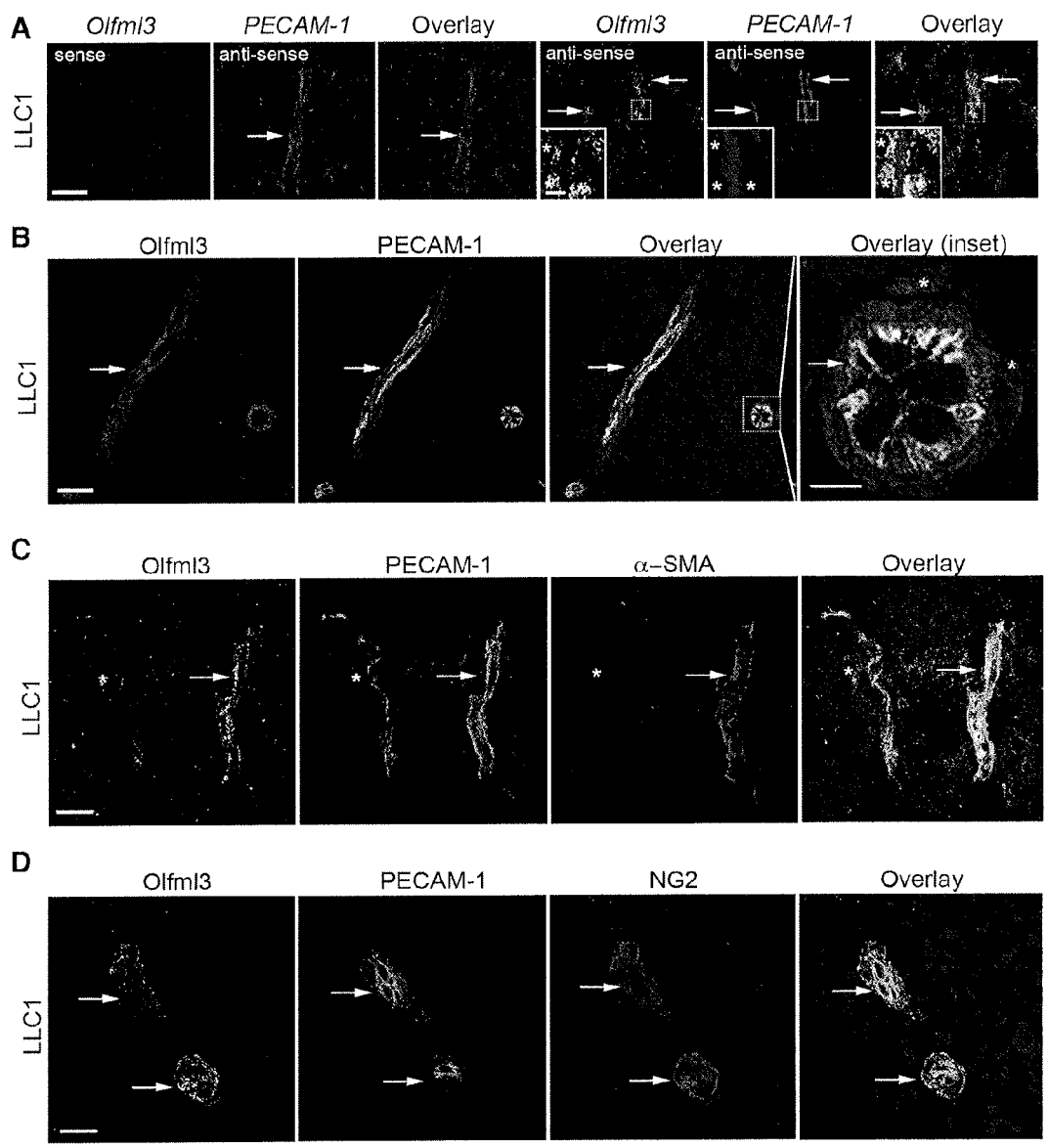
FIGS. 15A-E. Increased Olfml3 expression in tumor endothelial cells and pericytes.
Figure 15E:
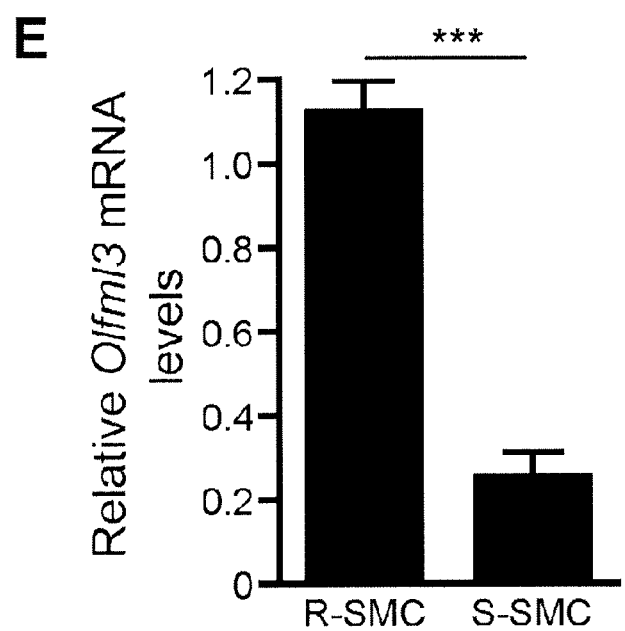
Figures 21A, 21B, 21C:
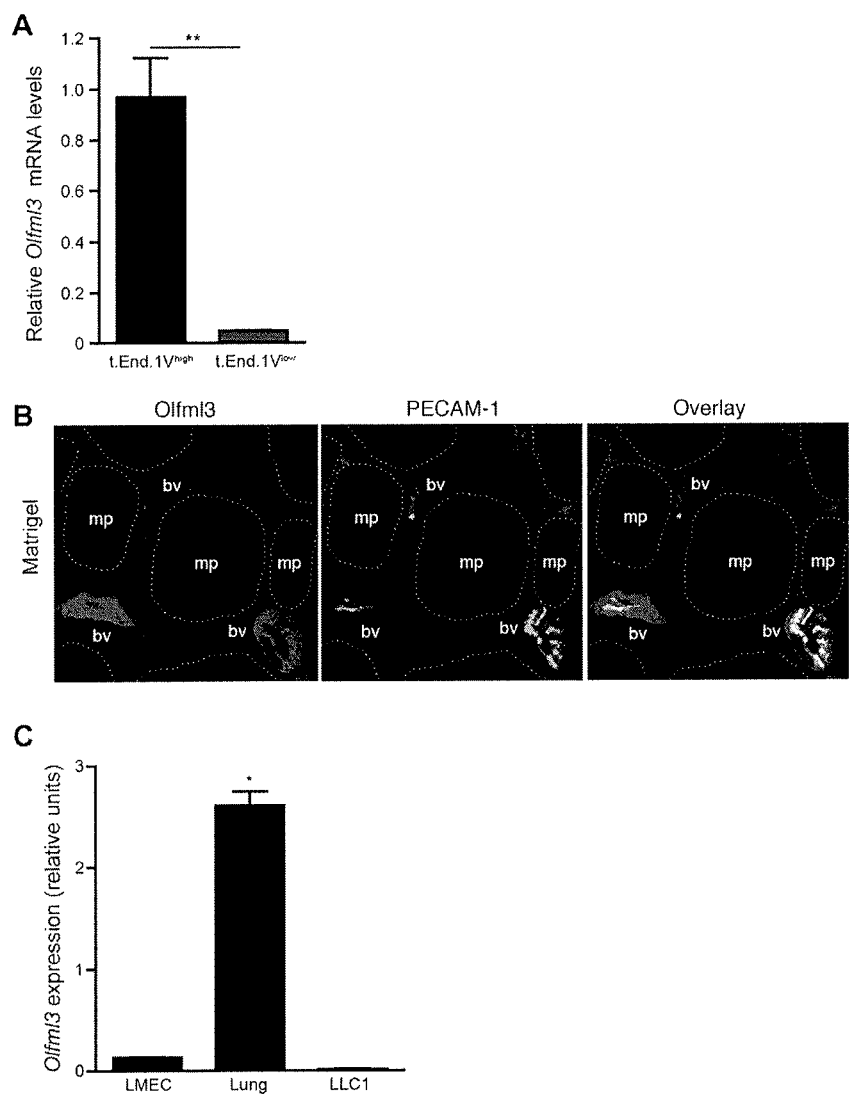
FIGS. 21A-C. Olfml3 is upregulated in angiogenic endothelium.

Following the transcriptome and histological analyses, Olfml3 expression was found to be restricted to angiogenic endothelial cells (t.End.1V$^{high}$) and vessels undergoing angiogenesis in matrigel plugs (FIGS. 21A-B). To evaluate Olfml3 expression in tumor angiogenic vessels, Lewis Lung Carcinoma (LLC1) cells were s.c. implanted in wild-type mice (FIG. 15). Transcripts of Olfml3 were detected in LLC1 tumor endothelium (PECAM-1$^+$) and accompanying pericytes (PECAM-Y) (FIG. 15A). Tumor cells themselves did not express Olfml3 mRNA (FIG. 21C). Double staining of tumors for Olfml3 and PECAM-1 revealed that Olfml3 protein is enriched in the extracellular space of endothelial cells and pericytes of a subset of tumor vessels (FIG. 15B). To validate vascular-specific Olfml3 expression, tumors were triple stained for Olfml3, PECAM-1, and the pericyte markers α-smooth muscle actin (α-SMA) or nerve/glial antigen-2 (NG2), respectively (FIGS. 15C, D). Olfml3 expression was detected in both α-SMA$^+$ and NG-2$^+$ pericytes, while was absent from α-SMA$^-$ pericytes (FIG. 15C). In order to determine whether Olfml3 is produced by pericytes on established, resting tumor vessels or de novo forming vessels, two different types of smooth muscle cells having pericyte-like characteristics (Brisset et al., 2007) were isolated. The actively proliferating and migrating cells (R-SMCs) expressed higher levels of Olfml3 compared with resting counterparts (S-SMCs) (FIG. 15E). Therefore, Olfml3 expression may correlate with the activation state of both endothelial cells and pericytes, implying a potential functional importance of Olfml3 during activation and maturation phases of angiogenesis.

Example 9

Autocrine Effects of Olfml3 on Endothelial Cells

Figures 16A, 16B, 16C:
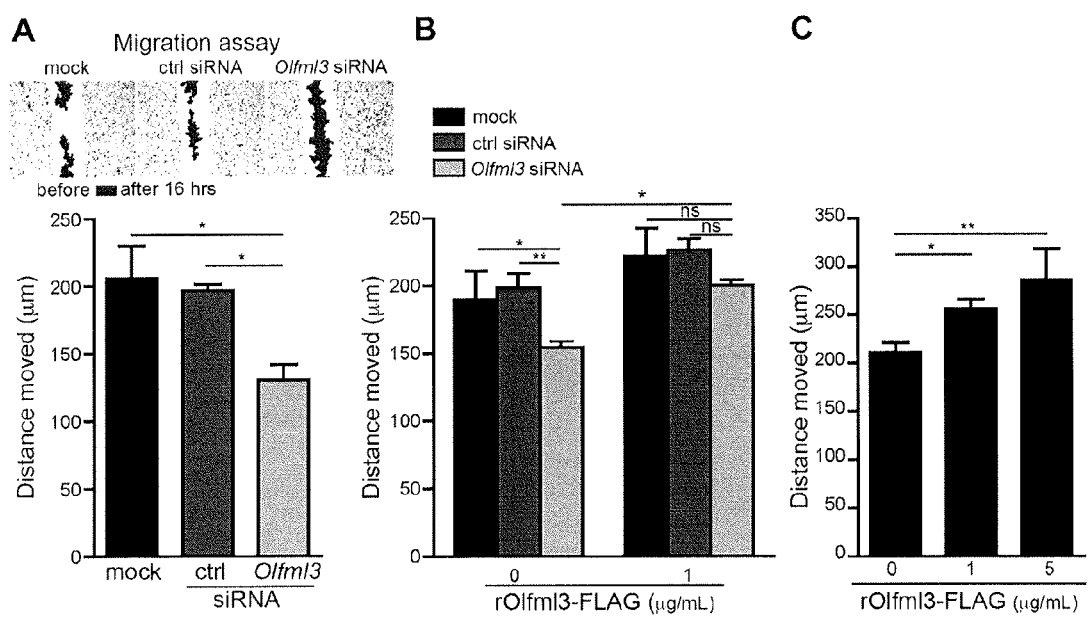
FIGS. 16A-F. Effects of Olfml3 targeting and rOlfml3-FLAG on t.End.1V$^{high}$ cell migration and sprouting.

To define the Olfml3-dependent vascular functions, the inventors first tested whether Olfml3 mediates endothelial cell migration. As t.End.1V$^{high}$ cells migrate efficiently in wound healing assays (Aurrand-Lions et al., 2004; Miljkovic-Licina et al., 2009), the inventors investigated the consequences of Olfml3 gene silencing (FIG. 22A) on the migration of t.End.1V$^{high}$ cells in this assay. The Olfml3-silenced t.End.1V$^{high}$ cells displayed a significantly decreased migration rate into the denuded area (FIG. 16A). Olfml3 silencing did not significantly affect endothelial cell proliferation (data not shown). This reduced migratory ability of Olfml3-silenced cells was partly compensated when recombinant Olfml3 FLAG-tagged protein (rOlfml3-FLAG) (FIG. 22B) was coated on plates (FIG. 16B). In addition, rOlfml3-FLAG promoted t.End.1V$^{high}$ cell migration in a concentration-dependent manner (FIG. 16C). These data identified Olfml3 as a novel autocrine regulator of endothelial cell migration.

Figures 16D, 16E, 16F:
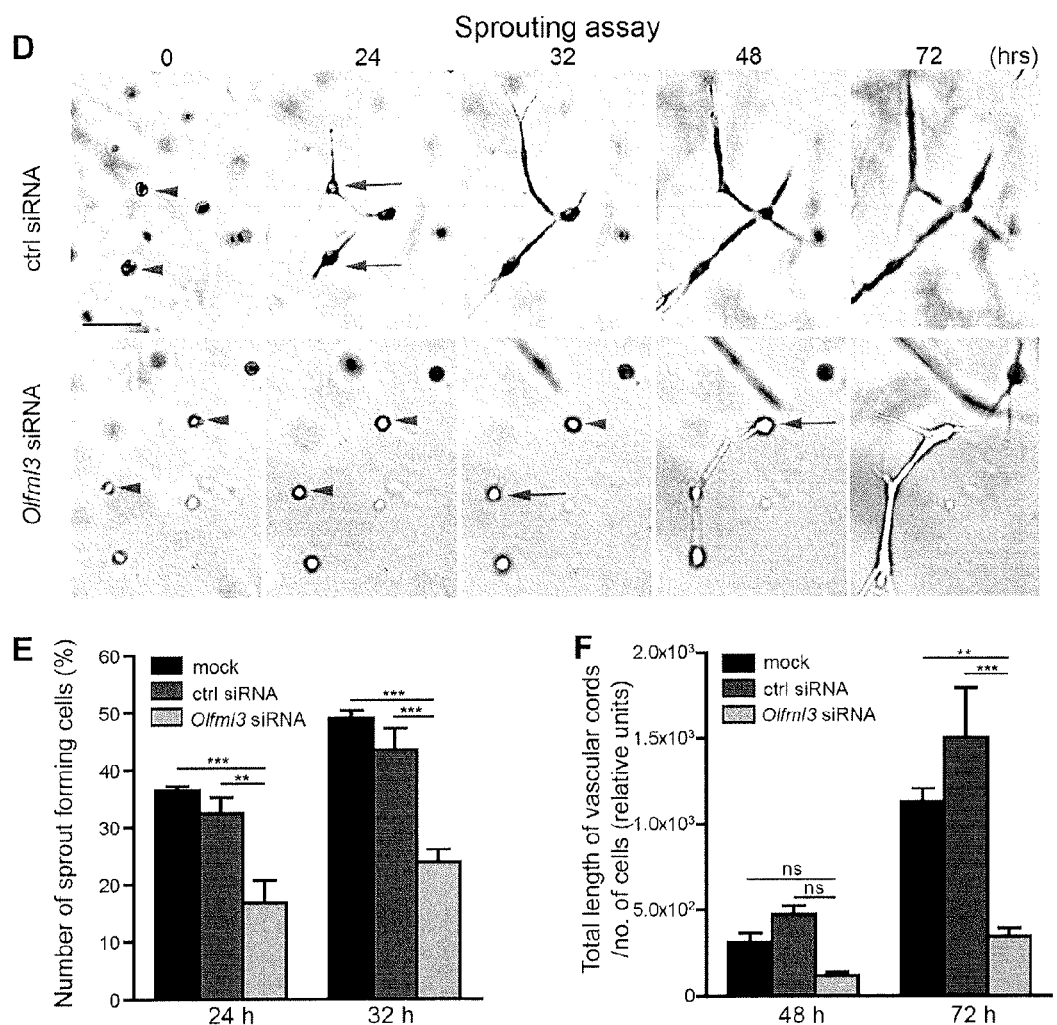
Figure 23:
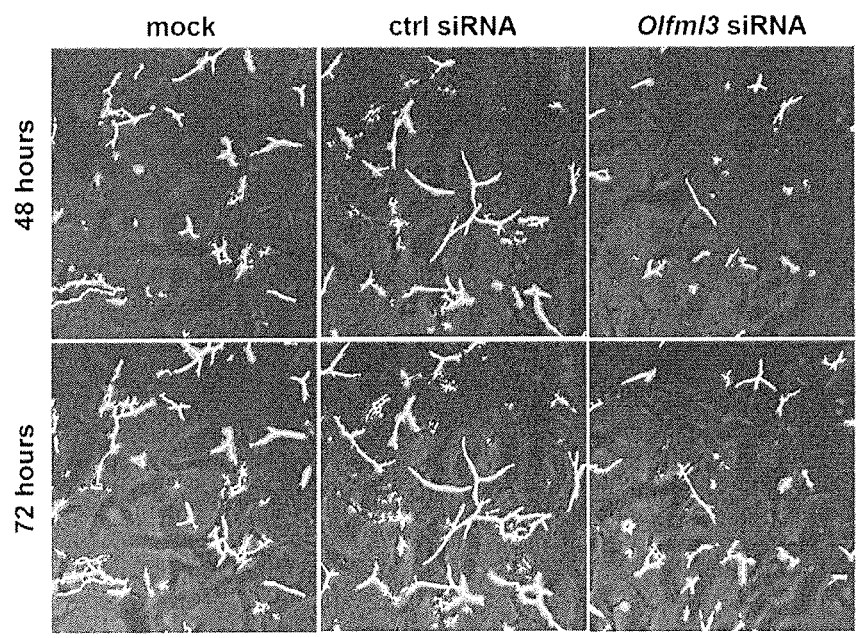
FIG. 23. In vitro t.End1.V$^{high}$ sprouting assays in 3D fibrin gels. Length and complexity of the vascular-like network of Olfml3-silenced t.End1.V$^{high}$ cells (Olfml3 siRNA, right panels) are reduced compared with mock (mock, left) or control siRNA-treated cells (ctrl siRNA, middle) at 48 and 72 hours of t.End1.V$^{high}$ sprouting in 3D fibrin gels.

The pro-migratory action of Olfml3 on t.End.1V$^{high}$ cells suggested that Olfml3 might also exert an effect on endothelial cell sprouting. As t.End.1V$^{high}$ cells efficiently form a capillary-like network of ramified cords in three-dimensional fibrin gels (Aurrand-Lions et al., 2004), the inventors used this assay to study the effect of Olfml3 depletion on t.End.1V$^{high}$ cell sprouting (FIGS. 16D-F). Compared with mock- or control siRNA-treated t.End.1V$^{high}$ cells (FIG. 16D), the number of Olfml3-silenced cells that initialized sprout protrusions at early time points (24-32 hours) was significantly decreased (FIG. 16D, E). In addition, total length of the vascular network in Olfml3-silenced cells was reduced drastically at later time points (72 hours) (FIG. 16F and FIG. 23). These findings suggest that abrogation of Olfml3 was sufficient to attenuate endothelial migration and sprouting, further supporting its potential role in angiogenesis.

Example 10

Anti-Olfml3 Antibodies Reduce LLC1 Tumor Growth and Angiogenesis

Figures 22A, 22B:
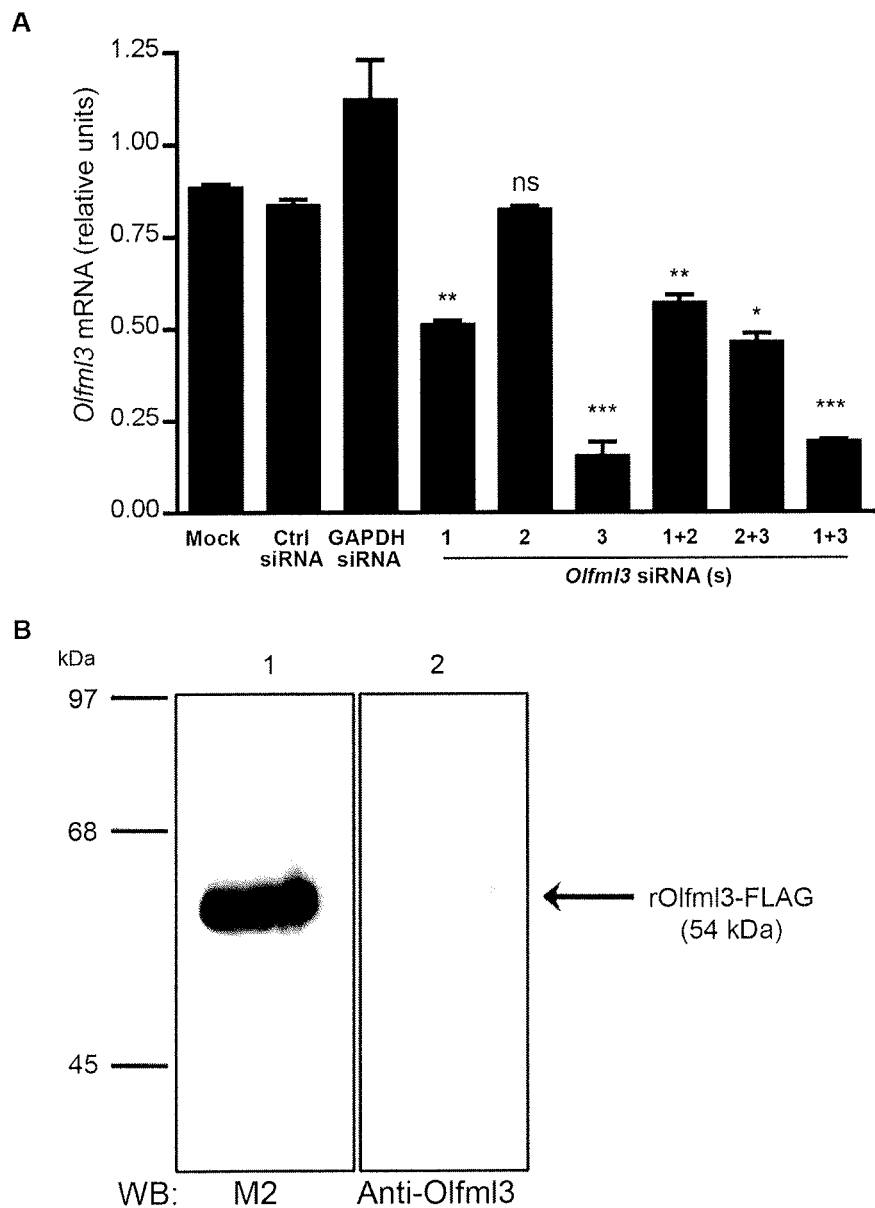
FIGS. 22A-B. Validation of Olfml3 down-regulation after siRNA delivery and production of rOlfml3 FLAG-tagged protein.

In order to test whether Olfml3 promotes tumor angiogenesis in vivo, the inventors generated rabbit anti-Olfml3 antibodies by injecting simultaneously two 13-aa long peptides comprising epitopes in the coiled-coil (peptide A) and the olfactomedin-like domains (peptide B) (FIG. 24A). Both peptides are identical in the mouse and human Olfml3 protein sequences (FIG. 24B). The anti-Olfml3 antibodies recognized the peptides A and B, respectively (FIG. 24C) as well as rOlfml3-FLAG (FIG. 22B).

Figures 17A, 17B:
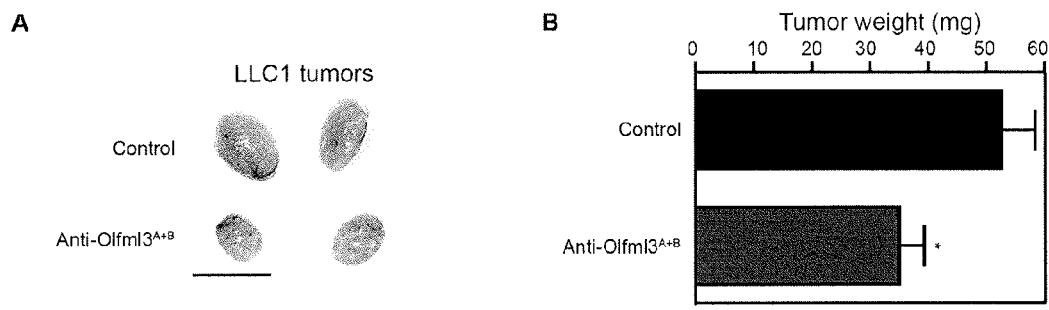
FIGS. 17A-F. Inhibitory effects of anti-Olfml3 antibodies on tumor growth and vascularization.
Figures 17C, 17D:
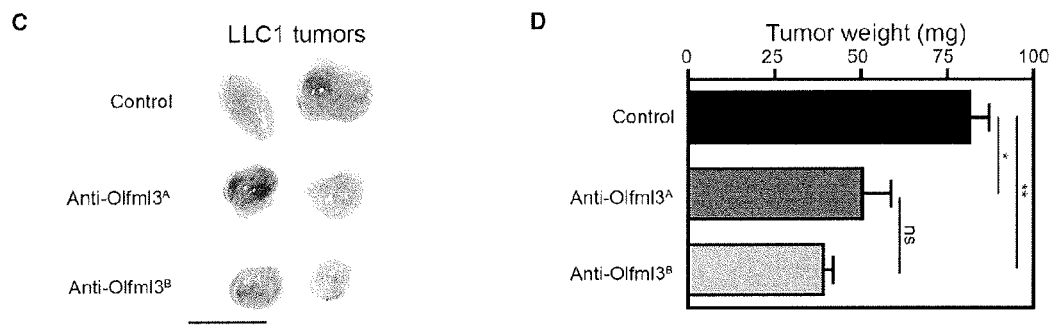
Figures 17E, 17F:
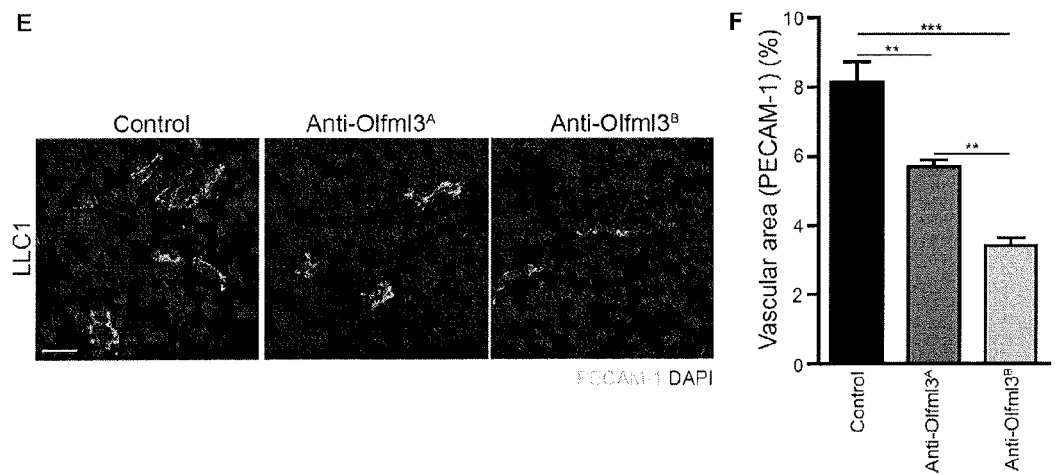

The Olfml3 antibodies were affinity-purified against both Olfml3 peptides (anti-Olfml3$^{A+B}$) and evaluated for the ability to block tumor growth and angiogenesis in the LLC1 mouse model. Treatment with anti-Olfml3$^{A+B}$ antibodies significantly decreased the tumor weight compared with control rabbit immunoglobulin G (IgG) treatment (FIGS. 17A, B). To determine which Olfml3 structural domain might be necessary for this effect, the inventors affinity-purified the Olfml3 antibodies against either the Olfml3 peptide A (anti-Olfml3$^A$) or peptide B (anti-Olfml3$^B$) and used them for the LLC1 tumor treatment. Both antibodies significantly reduced tumor growth by 38% and 52% respectively with no significant difference observed between either treatment (FIGS. 17C, D). The rate of tumor vascularization measured by PECAM-1 staining was significantly decreased by treatment with either anti-Olfml3$^A$ or anti-Olfml3$^B$ (FIGS. 17E, F). The antibodies showed different efficacy of reducing tumor vascularization. Anti-Olfml3$^B$ reduced tumor vascularization by 58%, whereas anti-Olfml3$^A$ had smaller but significant effect (30%), suggesting that both structural domains of the protein are necessary for its pro-angiogenic activity. However, when the two Olfml3 antibodies were co-injected, no synergistic inhibition of tumor vascularization was observed. These findings confirmed the hypothesis that Olfml3 promotes tumor angiogenesis, whereas blocking its function leads to reduced angiogenesis and tumor growth.

Example 11

Impaired Pericyte Coverage of Tumor Vessels after Anti-Olfml3 Treatment

Endothelial cell survival correlates with the extent of pericyte coverage in tumor vessels (Franco et al., 2011). As Olfml3 was co-expressed in tumor endothelial cells and accompanying pericytes (FIG. 1), the inventors investigated whether anti-Olfml3 antibodies affect pericyte coverage of tumor vessels using the pericyte marker α-SMA as the readout. Tumor blood vessels of control-treated mice exhibited abundant α-SMA$^+$ pericytes, while treatment with anti-Olfml3$^A$ or anti-Olfml3$^B$ dramatically reduced α-SMA immunoreactivity by 61.5 and 63%, respectively (FIGS. 18A, B). The observed effect could reflect a decrease in α-SMA expression by pericytes or a loss in the number of pericytes. To distinguish between these two possibilities, the inventors stained tumors for NG2, another pericyte marker (FIG. 18C). Numerous NG2$^+$ pericytes were observed under control conditions (FIGS. 18C, D). Following treatment with anti-Olfml3$^A$ or anti-Olfml3$^B$, however, NG2 immunoreactivity decreases substantially, by 67% and 78%, respectively (FIGS. 18C, D). These supporting observations indicate that the reduction in α-SMA immunoreactivity reflects a decrease in pericytes number rather than a decrease in α-SMA protein expression per cell. Therefore, targeting Olfml3 with its blocking antibodies decreases the pericyte coverage in tumor vessels, implying Olfml3 involvement in the maturation of de novo-forming vasculature.

Example 12

Olfml3 is a BMP4-Binding Protein

Figures 19A, 19B:
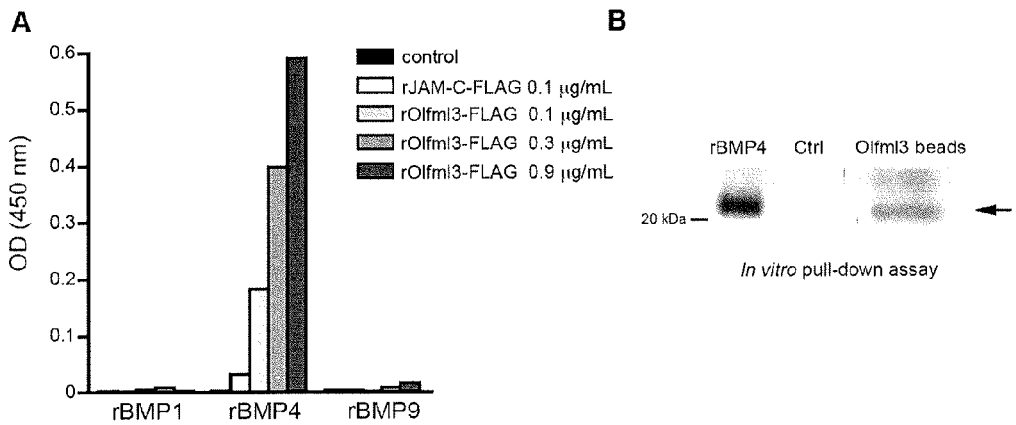
FIGS. 19A-E. Recombinant Olfml3 binds rBMP4.
Figures 19C, 19D, 19E:
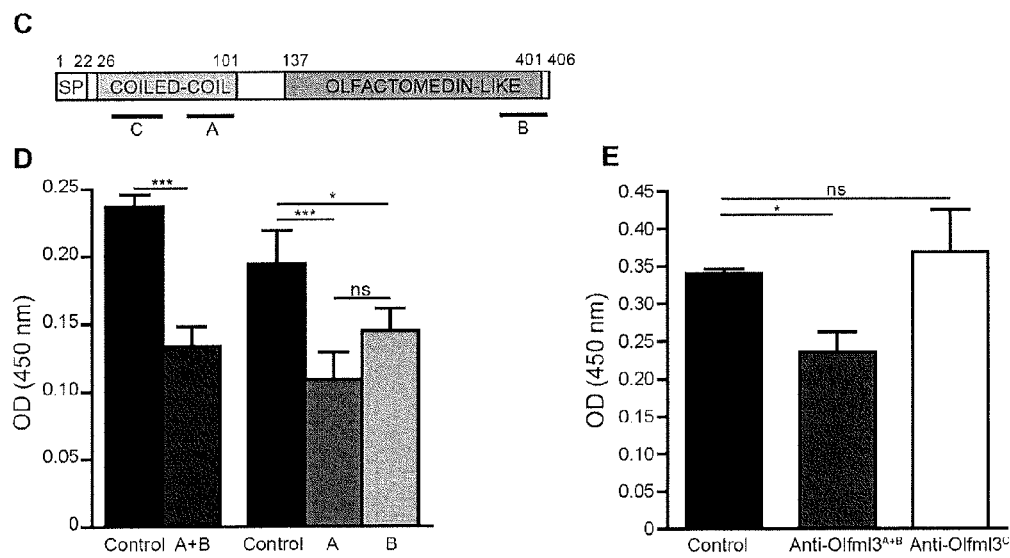

Previous studies have shown that *Xenopus* Olfml3 interacts with BMP1 and chordin through the coiled-coil and olfactomedin-like domains, respectively (Inomata et al., 2008). The inventors therefore investigated a possible interaction of Olfml3 with BMPs known as either pro- or anti-angiogenic cues within the tumor microenvironment (David et al., 2009). The inventors used rOlfml3-FLAG for interaction studies with three different BMPs in enzyme-linked immunosorbent assays. rOlfml3-FLAG specifically bound recombinant BMP4 (rBMP4) but not rBMP1 or rBMP9 (FIG. 19A), and rOlfml3-FLAG co-immunoprecipitated with rBMP4 (FIG. 19B). To map the BMP4-binding regions on the Olfml3 protein, anti-Olfml3$^A$, anti-Olfml3$^B$ and a commercial antibody raised against a distinct Olfml3 peptide (Olfml3 peptide C) were used for binding studies (FIG. 19C). Both anti-Olfml3$^A$ and anti-Olfml3$^B$ antibodies blocked the interaction of rOlfml3-FLAG with rBMP4 (FIG. 19D). The third high-affinity antibody, targeting a non-overlapping epitope in the coiled-coiled domain, did not block Olfml3-BMP4 interaction (FIG. 19E). These results suggest that the coiled-coil (peptide A) and the olfactomedin-like domain (peptide B) are equally required for the interaction with BMP4, confirming the previous hypothesis of a single ligand for the two Olfml3 domains. The results define a novel interaction between mouse Olfml3 and BMP4, a potent pro-angiogenic growth factor.

Example 13

Olfml3 Activates Canonical SMAD1/5/8 Signaling Pathway in HUVECs

Figure 20A:
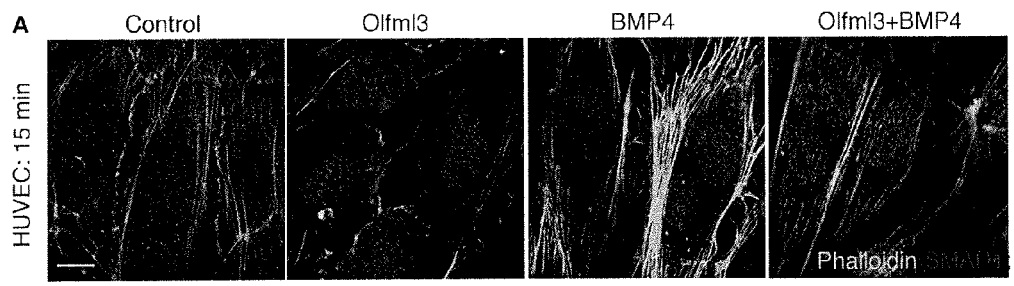
FIGS. 20A-D. Olfml3 activates the canonical SMAD1/5/8 pathway.
Figure 20B:
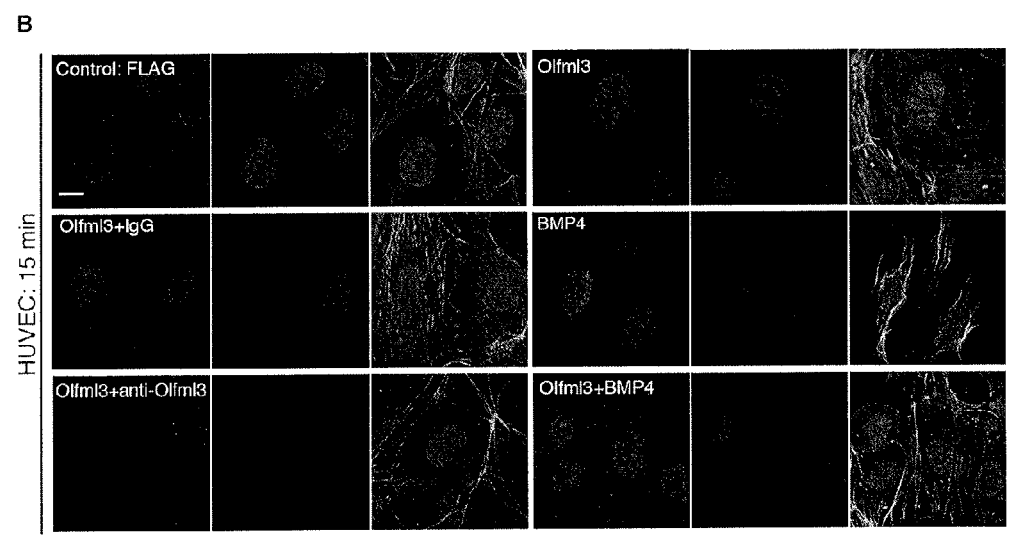
Figures 20C, 20D:
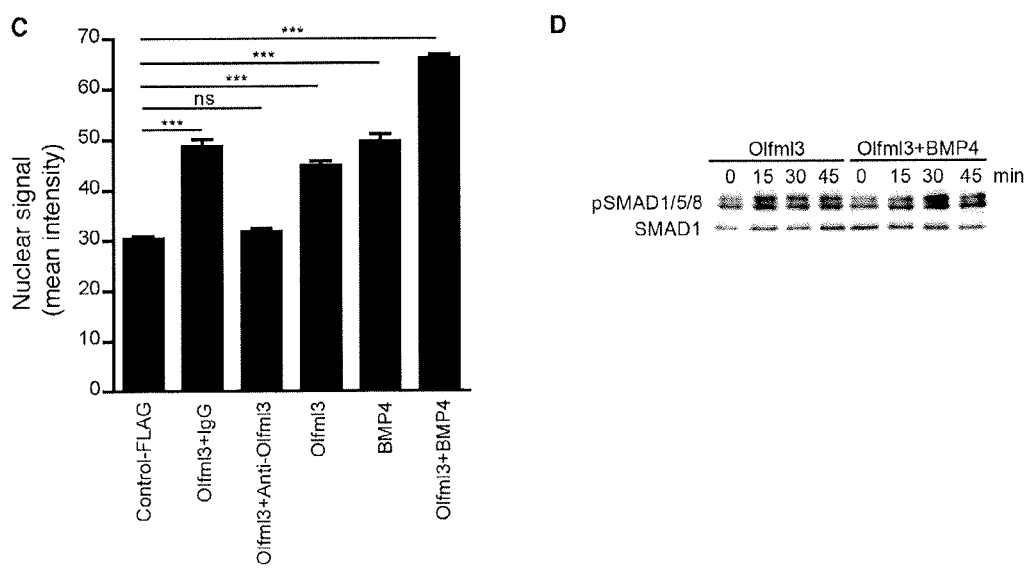

As BMP4 directly binds to Olfml3 (FIG. 19), the inventors sought to investigate the possible effect of this interaction in BMP4 downstream signaling. HUVECs were treated with rOlfml3-FLAG and/or BMP4 and subsequently both nuclear translocation of SMAD1 and phosphorylation of SMAD1/5/8 as readouts of the BMP4 pathway activity were analyzed (FIG. 20). rOlfml3-FLAG alone induced nuclear translocation of SMAD1 after 15 minutes (FIG. 20A). Likewise, nuclear translocation of SMAD1 was observed in BMP4-treated HUVECs (FIG. 20A). Upon challenge of HUVECs with rOlfml3-FLAG or BMP4, Smad1/5/8 proteins were phosphorylated rapidly (FIGS. 20B-D), whereas SMAD1/5/8 phosphorylation was not observed in untreated control cells (data not shown) or cells treated with the FLAG peptide (FIGS. 20B, C). In the presence of anti-Olfml3$^{A+B}$ antibodies, the ability of Olfml3 to induce SMAD1/5/8 phoshorylation is lost (FIGS. 20B, C). Of interest, Olfml3 and BMP4 showed additive effects on pSMAD1/5/8 phosphorylation when combined (FIGS. 20B-D). While SMAD1/5/8 phosphorylation reached a maximum after 15 minutes of rOlfml3-FLAG exposure in HUVECs (FIG. 20D), rOlfml3-FLAG and BMP4 exposure gave rise to an increased and prolonged effect on SMAD1/5/8 phosphorylation in time course experiments (FIGS. 20C, D). These findings demonstrate that Olfml3 alone or in a complex with BMP4 acts as an enhancer of the SMAD1/5/8 signaling pathway in HUVECs.

Example 14

Anti-Olfml3 Monoclonal Antibodies Reduce Tumor Growth

Figure 25A:
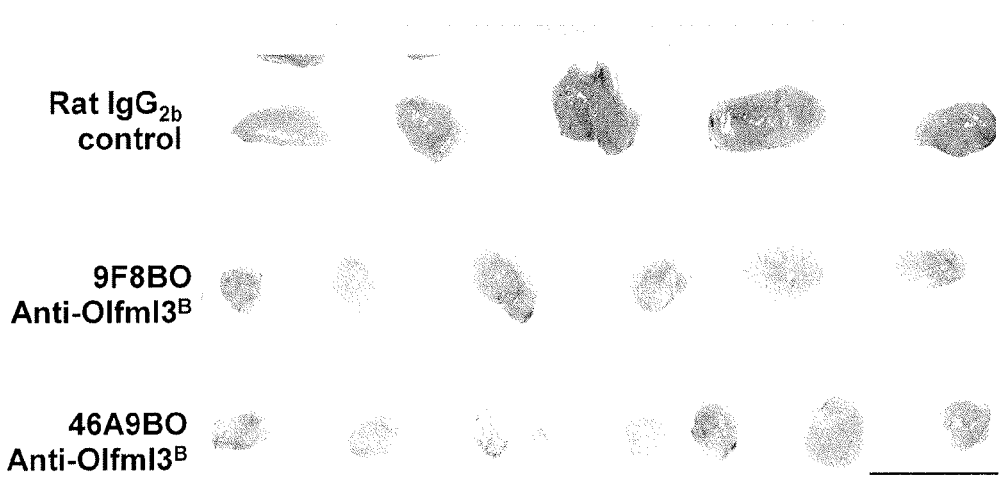
FIGS. 25A-B. Inhibitory effects of rat monoclonal antibodies against human Olfml3 on tumor growth.
Figure 25B:
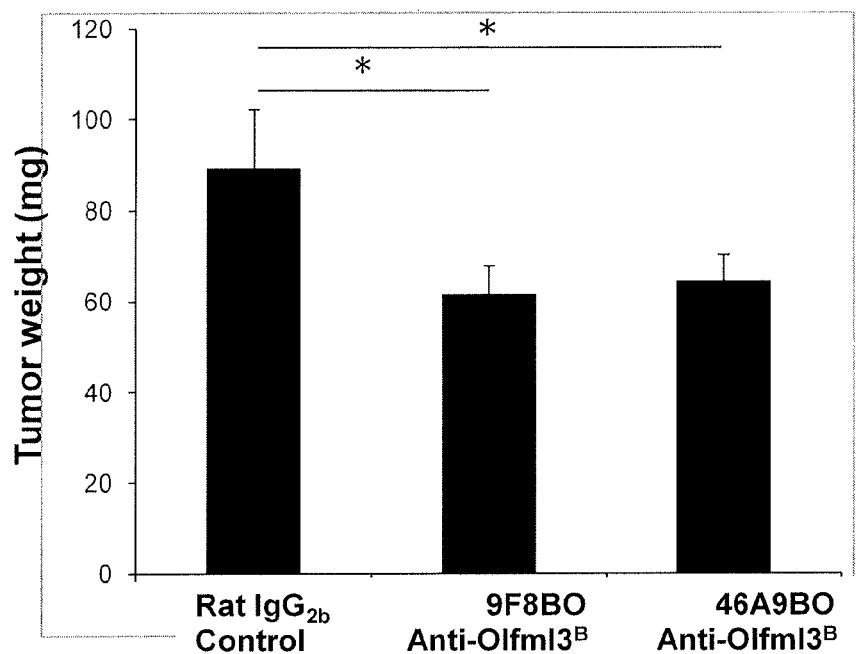

Two rat monoclonal antibodies that recognize peptide B (390-403 aa of human/mouse Olfml3) reduced tumor growth by half (FIGS. 25A-B). The mice were injected with LLC1 tumor cells and treated with novel anti-Olfml3 monoclonal antibodies over several days. Two out of three tested anti-Olfml3 peptide B monoclonal antibodies substantially reduced the size of the tumor and the number of blood vessels as the tumor tissue appears white (anaemic). Interestingly there is a non-functional anti-Olfml3$^B$ mAb against peptide B that can serve as control. This also suggests that a subdomain of peptide B represents the active epitope.

Example 15

Materials and Methods

Cell Lines and Culture t.End.1V$^{high}$ cells were maintained as described previously (Aurrand-Lions et al., 2004). Lewis lung carcinoma cells (LLC1; European Collection of Cell Cultures) were cultured in DMEM (Life Technologies), supplemented with 10% FBS. Smooth muscle cells (SMCs) were isolated from the media of porcine carotid artery using enzymatic digestion (S-SMCs) or tissue explanation (R-SMCs) as described previously (Brisset et al., 2007). HUVECs were isolated freshly and cultured in EGM-2 Bulletkit (Lonza).

Tumor Model

All studies were conducted in accordance with the ethical approval and recommendations of the Veterinary Office of Geneva state, according to the Swiss federal law. To generate an implantation tumor model, a suspension of 0.5×10$^6$ LLC1 tumor cells in 100 µL PBS was implanted subcutaneously into the flank of female C56BL/6J mice (8-10 weeks old). Mice were then treated with 25-50 µg of control, total rabbit IgG; 50 µg of anti-Olfml3$^{A+B}$ affinity-purified against both Olfml3 peptides, and 25 µg of anti-Olfml3 or anti-Olfml3$^B$ affinity-purified against each peptide i.p. every third day starting from day 1. When tumors reached an average size of 1 cm, mice were sacrificed and tumors were harvested for evaluation of tumor growth.

In Situ mRNA Hybridization

The digoxigenin- and fluorescein-labeled (Roche) RNA probes were prepared after PCR amplification of mouse PECAM-1 and Olfml3 genes as described in Supplementary Methods. In situ mRNA hybridization was performed on frozen sections of LLC1 tumors as previously described (Miljkovic-Licina et al., 2009).

Immunohistochemistry

HUVECs were grown on glass slides and immunohistochemistry was performed as detailed in Supplementary Methods. LLC1 tumors were processed for and stained by immunohistochemistry as previously described (Miljkovic-Licina et al., 2009). Samples were incubated with: rabbit anti-Olfml3$^{A+B}$ serum, rat monoclonal anti-PECAM-1 (Piali et al., 1993), mouse anti-α-SMA (Brisset et al., 2007) or mouse monoclonal anti-NG2 (clone 132.38; Millipore). Quantification of relative vascular and pericyte areas was performed using Metamorph6.0 (Molecular Devices). Ten individual images at three section planes were analyzed in 8-10 tumors/group (4-5 mice/group) in 2-3 independent experiments. Relative vascular and pericyte area were measured as the ratios of the total pixel counts of PECAM-1, α-SMA or NG2 to DAPI staining.

In Vitro Wound Healing Assay

Transient transfection of t.End.1V$^{high}$ cells was performed using Amaxa™ Nucleofector (Lonza) with Stealth™ Select siRNAs (Life Technologies) as described in Supplementary Methods. The efficiency of Olfml3 silencing in t.End.1V$^{high}$ cells was evidenced by RT-qPCR. Transfected t.End.1V$^{high}$ cells (1.5×10$^4$) were seeded onto matrigel- or rOlfml3-FLAG-coated (BD Biosciences) plates and in vitro wound healing assays were performed as described previously (Miljkovic-Licina et al., 2009).

In Vitro Sprouting Assay

Transfected t.End.1V$^{high}$ cells (1.2×10$^4$ cells/gel) were seeded in suspension into fibrin gels (Pepper et al., 1996) and in vitro sprouting assays were performed as described previously (Miljkovic-Licina et al., 2009).

Enzyme-Linked Immunosorbent Assay (ELISA)

Maxisorb immunoplates (Nunc) were coated overnight at 4° C. with rBMP4 (2 µg/mL). Wells were washed, blocked with 1% BSA, and incubated with rOlfml3-FLAG at 0.5 µg/mL in PBS containing 0.05% Tween 20 and 0.5% BSA. Biotinylated M2 antibody (2 µg/mL) was added. Bound M2 was detected using streptavidin-HRP (Jackson Immunoresearch Laboratories) and substrate Reagent Pack (R&D Systems). Optical densities at 450 nm were read using a kinetic microplate reader and SoftMAXPro (Molecular Devices).

Pull-Down Assay of rBMP4 by rOlfml3-Flag rBMP4 (R&D Systems) was incubated at 4° C. with anti-FLAG M2-Agarose beads (Sigma-Aldrich) loaded with or without rOlfml3-FLAG (1 µg) in TBS, 0.1% NP-40, 0.05% BSA. Beads were eluted with non-reducing SDS sample buffer. Samples were further subjected to SDS-PAGE and silver staining was performed using SilverQuest staining kit (Invitrogen).

Western Blotting

HUVECs were serum-starved in OptiMEM (Invitrogen) and 50 ng/mL rBMP4 (R&D Systems) and/or 50 ng/mL of rOlfml3-FLAG were added. Cells were lysed with lysis buffer [50 mM Tris-HCl (pH 7.4), 150 mM NaCl, 10 mM MgCl2 and 0.5% Triton X-100] containing a cocktail of protease and phosphatase inhibitors (Sigma-Aldrich). Blots were incubated with anti-phosphoSMAD1/5/8 or anti-SMAD1 (Cell Signaling Technology) and revealed using the HRP-labeled anti-rabbit antibodies (Jackson ImmunoResearch Laboratories), visualized using an enhanced chemiluminescence system and a quantitative imaging system Fujifilm LAS4000Mini (Fujifilm).

In Situ mRNA Hybridization

The digoxigenin (DIG)- and fluorescein (FLUO)-labeled (Roche) RNA probes were prepared after PCR amplification of mouse PECAM-1 and Olfml3 genes using corresponding forward and reverse primers containing the T7 polymerase binding site (underscored) for sense or antisense RNA probes, as follows: PECAM-1-sense-for1, 5'-CTAATAC-GACTCACTATAGGGATGCTCCTGGCTCTGGGACTC-3' (SEQ ID NO:5); PECAM1-sense-rev 1, 5'-TGCAGCTG-GTCCCTTCTATG-3' (SEQ ID NO:6); PECAM-1-anti-sense-for1, 5'-ATG CTC CTG GCT CTG GGA CTC-3' (SEQ ID NO:7); PECAM-1-antisense-rev1, 5'-CTAATACGACT-CACTATAGGG TGC AGC TGG TCC CCT TCT ATG)-3' (SEQ ID NO:8); Olfml3-sense-for1, 5'-CTAATACGA-CTCACTATAGGGAGT GCT CCT CTG CTG CTC CTC-3' (SEQ ID NO:9); Olfml3-sense-rev1, 5'-CGT GTC GTT CTG GGT GCC GTC-3' (SEQ ID NO:10); Olfml3-antisense-for1, 5'-AGT GCT CCT CTG CTG CTC CTC-3' (SEQ ID NO:11); and mOlfml-3-antisense-rev1, 5'-CTAATACGACTCACTA-TAGGGCGT GTC GTT CTG GUT GCC GTC-3' (SEQ ID NO:12).

siRNA Delivery

The following chemically modified duplex siRNAs were engaged: three siRNAs directed against non-overlapping regions of the mouse Olfml3 gene (OLFML3MSS235376, OLFML3MSS235377, and OLFML3MSS235378, named as O μm/3 siRNA 1, 2, and 3, respectively), a siRNA against mouse GAPDH, and a non-targeting negative control siRNA (ctrl siRNA) (Stealth™ Select Technology; Life Technologies). Single siRNAs or combinations of two siRNAs were transfected in the t.End.1V$^{high}$ cells at the concentration of 0.5 μM using Amaxa™ Nucleofector technology (Lonza). The efficiency of Olfml3 silencing in t.End.1V$^{high}$ cells was evidenced by real-time qPCR 24-72 h after transfection.

Quantitative Real-Time PCR

Total RNA was extracted from following cells: t.End1.V$^{high}$, LLC1, LMEC, R-SMC, S-SMC and murine lung tissue using the RNeasy Mini Kit (Qiagen). The purified RNA was quantified at 260 nm and RNA quality was evaluated by capillary electrophoresis on an Agilent 2100 Bioanalyzer (Agilent Technologies). Total RNA was reverse transcribed using the cDNA synthesis kit (Roche). Primers used for real-time qPCR were as follows: mouse Olfml3_for1, 5'-GCTGTCTATGCCACTCGAGATG-3' (SEQ ID NO:13) (forward) and Olfml3_rev1, 5'-TGTGTCAAGTGTCT-GTGGGTCTAA-3' (SEQ ID NO:14) (reverse); human Olfml3, 5'-GTCTATGCCACCCGGGAGGAT-3'*SEQ ID NO:15) (forward) and Olfml3 rev1, 5'-TGTGTCCAGT-GTCTGTGGATCTAA-3' (SEQ ID NO:16). Reactions were performed in triplicate with the Power SYBR Green PCR kit and primers were assayed on an ABI Prism 7900 FIT (Applied Biosystems). Raw threshold cycle (ct) values were obtained using SDS2.2 software (Applied Biosystems) and the normalization factor and fold changes were calculated using three mouse reference genes (β-actin, β-tubulin and EEF1A1) or a porcine GAPDH reference gene, according to the GeNorm method (Carmeliet and Jain, 2011).

Cloning Strategy for Production of Recombinant Olfml3 Protein Tagged with a FLAG Sequence The full-length Olfml3 cDNA was obtained by PCR performed on the pCMV-SPORT6 vector (Invitrogen) containing the Olfml3 clone (ID3485412) from the MGC cDNA library (NIH). The Olfml3 PCR fragment was cloned into the pcDNA3.1 (Invitrogen) vector containing a FLAG sequence, where a FLAG sequence was inserted downstream to and in-frame with the Olfml3 coding sequence. The Olfml3-FLAG PCR fragment was then inserted into the pcDNA3.3 TOPO TA vector (Invitrogen). The plasmid was multiplied in DH5α Escherichia coli, purified using EndoFree Plasmid maxi preparation (Qiagen), and used for production of the recombinant protein.

Production and Purification of Mouse Recombinant Olfml3-FLAG Tagged Protein (rOlfml3-FLAG)

The expression vector pcDNA3.3 TOPO TA (Invitrogen) with Olfml3-FLAG sequence was used for transient transfection of human HEK-293 cell line in a serum-free suspension, as described previously (Folkman, 2007). The cell culture supernatants were collected and rOlfml3-FLAG was affinity-purified using anti-FLAG M2 agarose beads (Sigma-Aldrich), eluted with FLAG peptide (100 μg/mL; Sigma-Aldrich). Next, 0.1 μg of rOlfml3-FLAG was subjected to sodium dodecyl sulfate-polyacrylamide gel electrophoresis (SDS-PAGE), blotted on nitrocellulose, and revealed either with biotinylated FLAG antibody in combination with streptavidin-HRP conjugate or rabbit anti-Olfml3 antibody revealed with the anti-rabbit HRP labeled antibodies (Jackson ImmunoResearch Laboratories), visualized using an enhanced chemiluminescence system (GE Healthcare).

Generation of Rabbit Anti-Mouse Olfml3 Polyclonal and Monoclonal Rat Anti-Human/Mouse Antibodies Polyclonal antibodies against mouse Olfml3 were generated by immunizing rabbits with Olfml3 synthetic peptide A (86-99) and peptide B (390-403) (Covalab, France). The rabbit sera were then tested for reactivity. Antibodies were purified from serum by affinity chromatography against peptide A and B or each peptide separately. Fischer rats were immunized with human peptide B mixed with Titermax adjuvant (Sigma) and LN B cells and splenocytes were fused to Sp2/0 cells. Hybridomas were then selected in HAT-containing medium and resistant clones screened by ELISA for the production of mAbs against peptide B and recombinant Olfml3. Antibodies recognized human and mouse peptides.

FGF2-Loaded Matrigel Plug Assay

Eight-week-old female C57BL6/J mice were injected subcutaneously with matrigel (400 μL per animal, BD Biosciences) supplemented with the angiogenic growth factor FGF2 (500 ng/mL per animal; Peprotech) into C57BL/6J mice. After 8 days, the plugs were excised and prepared for immunohistological evaluation.

Immunohistochemistry

HUVECs grown to 80% confluence on glass slides were serum starved for 2 h in OptiMEM (Invitrogen) and treated with 50 ng/mL of BMP4 (R&D Systems) and/or 100 ng/mL of rOlfml3-FLAG for indicated times. As controls, HUVECs were incubated with 500 ng/mL of FLAG peptide (Sigma-Adrich) and 100 ng/mL of rOlfml3-FLAG in the presence of rabbit total IgG or anti-Olfml3$^{A+B}$ serum. HUVECs were fixed in 4% para-formaldehyde for 20 min at room temperature, washed in phosphate buffered saline (PBS) and permeabilized in 0.1% sodium citrate, 0.1% Triton X-100 for 2 min on ice. Cells were then washed in PBS and saturated in 1% bovine serum albumin and 2% donkey serum in PBS for 1 h at room temperature. For detection, glass slides were incubated with: rabbit anti-SMAD1 or anti-phosphoSMAD1/5/8 antibodies (Cell Signaling Technology), for 1 h at room temperature. Unbound antibodies were removed using 0.1% Tween 20 in PBS. Rabbit anti-SMAD1 or anti-phosphoSMAD1/5/8 antibodies were detected using donkey anti-rabbit IgG coupled to rhodamine (Jackson ImmunoResearch Laboratories). Samples were stained for FITC-Phalloidin (Sigma-Aldrich) and mounted as described above. Quantification of nuclear phosphoSMAD1/5/8 staining was quantified using Metamorph6.0 software (Molecular Devices) and mean intensity was measured from at least five random microscopic fields for each group in three independent experiments.

Statistical Analysis

All data are presented as means±standard deviation (SD) unless indicated otherwise. For comparisons of two means, Student's t-test (2-sided, paired) was used. For multiple mean comparisons, one-way or two-way ANOVA followed by the Bonferroni's test was used. All statistical computations were done using GraphPadPrism. Results were considered statistically significant at $P<0.05$.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,816,567
U.S. Pat. No. 4,867,973
U.S. Pat. No. 4,870,287
U.S. Pat. No. 4,938,948
U.S. Pat. No. 4,946,778
U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052
U.S. Pat. No. 5,656,434
U.S. Pat. No. 5,739,169
U.S. Pat. No. 5,760,395
U.S. Pat. No. 5,770,376
U.S. Pat. No. 5,789,208
U.S. Pat. No. 5,801,005
U.S. Pat. No. 5,821,337
U.S. Pat. No. 5,824,311
U.S. Pat. No. 5,830,880
U.S. Pat. No. 5,844,091
U.S. Pat. No. 5,846,945
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259
U.S. Pat. No. 6,861,572
U.S. Pat. No. 6,875,434
U.S. Pat. No. 6,881,557
U.S. Pat. No. 6,891,024
U.S. Pat. No. 6,946,546
U.S. Pat. No. 7,122,181
U.S. Publn. 2002/0172677
U.S. Publn. 2004/0126828
U.S. Publn. 20050214860
Astorga and Carlsson, *Development*, 134(20):3753-3761, 2007.
Aurrand-Lions et al., *J. Pathol.*, 203:700-709, 2004.
Austin-Ward and Villaseca, *Revista Medica de Chile*, 126(7): 838-845, 1998.
Balemans and Van Hul, *Dev. Biol.*, 250(2):231-250, 2002.
Bangham et al. *J. Mol. Biol.*, 13(1):238-252; 253-259, 1965.
Barbas et al., *Proc. Natl. Acad. Sci., USA*, 91:3809-3813, 1994.
Brisset et al., *Circ. Res.*, 100:1055-1062, 2007.
Bukowski et al., *Clinical Cancer Res.*, 4(10):2337-2347, 1998.
Carmeliet and Jain, *Nature*, 473:298-307, 2011.
Carmeliet, *Nat. Med.*, 9:653-660, 2003,
Carmeliet, *Nature*, 438:932-936, 2005.
Celeste et al., *Proc. Natl. Acad. Sci. USA*, 87(24):9843-9847, 1990.
Cherqui et al., *Mol. Ther.*, 15:1264-1272, 2007.
Christodoulides et al., *Microbiology*, 144(Pt 11):3027-3037, 1998.
Crawford and Ferrara, *Trends Pharmacol. Sci.*, 30:624-630, 2009.
David et al., *Cytokine Growth Factor Rev.*, 20:203-212, 2009.
Davidson et al., *J. Immunother.*, 21(5):389-398, 1998.

Deamer and Uster, In: *Liposome Preparation: Methods and Mechanisms*, Ostro (Ed.), Liposomes, 1983.
Drake and Fleming, *Blood,* 95(5):1671-1679, 2000.
Ferris et al., *Arch. Ophthalmol.,* 102(11):1640-1642, 1984.
Folkman, *J. Pediatr. Surg.,* 42:1-11, 2007.
Folkman, *N. Engl. J. Med.,* 285:1182-1186, 1971.
Folkman, *Nat. Med.,* 1:27-31, 1995.
Franco et al., *Blood,* 118:2906-2917, 2011.
Gariano and Gardner, *Nature,* 438:960-966, 2005.
Gerhardt et al., *Cell Tissue Res.,* 314(1):15-23, 2003.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gram et al., *Proc. Natl. Acad. Sci. USA,* 89:3576-3580, 1992.
Gregoriadis, In: *Drug Carriers in Biology and Medicine,* Gregoriadis (Ed.), 287-341, 1979.
Hanahan and Weinberg, *Cell,* 144:646-674, 2011.
Hanahan, *Science,* 277:48-50, 1997.
Flanibuchi et al., *Int. J. Cancer,* 78(4):480-485, 1998.
Hellstrand et al., *Acta Oncologica,* 37(4):347-353, 1998.
Hu et al, *Cancer Res.,* 56:3055-3061, 1996.
Hui and Hashimoto, *Infection Immun.,* 66(11):5329-5336, 1998.
Ikeya et al., *Int. J. Dev. Biol.,* 49(7):807-823, 2005.
Inomata et al., *Cell,* 134:854-865, 2008.
Ju et al., *Gene Ther.,* 7(19):1672-1679, 2000.
Kaneda et al., *Science,* 243:375-378, 1989.
Kato et al, *J. Biol. Chem.,* 266:3361-3364, 1991.
Khankin et al., *Semin. Thromb. Hemost.,* 36(3):309-320, 2010.
Klein et al., *Arch. Ophthalmol.,* 102:520-526, 1984.
Langenfeld and Langenfeld, *Mol. Cancer. Res.,* 2(3):141-149, 2004.
Marks et al., *Bio/Technol.,* 10:779-783, 1992.
Miljkovic-Licina et al., *FASEB J.,* 23(12):4105-4116, 2009.
Mitchell et al., *Ann. NY Acad. Sci.,* 690:153-166, 1993.
Mitchell et al., *J. Clin. Oncol.,* 8(5):856-869, 1990.
Montesano et al., *Cell,* 62:435-445, 1990.
Moreno-Miralles et al., *Curr. Opin. Hematol.,* 16(3):195-201, 2009.
Morikawa et al., *Am. J Pathol.,* 160(3):985-1000, 2002.
Morton et al., *Arch. Surg.,* 127:392-399, 1992.
Nicolau et al., *Methods Enzymol.,* 149:157-176, 1987.
Oelgeschlager et al., *Nature,* 405:757-763, 2000.
Pepper et al., *Enzyme Protein,* 49:138-162, 1996.
Piali et al., *Eur. J. Immunol.,* 23:2464-2471, 1993.
Pietras et al., *Oncogene,* 17(17):2235-2249, 1998.
Potente et al., *Cell,* 146:873-887, 2011.
Qin et al., *Proc. Natl. Acad. Sci. USA,* 95(24):14411-14416, 1998.
Raida et al., *Int. J. Mol. Med.,* 18(4):735-739, 2006.
Raida et al., *J. Cancer Res. Clin. Oncol.,* 131(11):741-750, 2005.
Ravindranath and Morton, *Intern. Rev. Immunol.,* 7: 303-329, 1991.
Remington: The Science and Practice of Pharmacy, $21^{St}$ Ed. Lippincott Williams and Wilkins, 2005.
Rosen, *Ann. NY Acad. Sci.,* 1068:19-25, 2006.
Rosenberg et al., *Ann. Surg.* 210(4):474-548, 1989.
Rosenberg et al., *N. Engl. J. Med,* 319:1676, 1988.
Rothhammer et al., *Oncogene,* 26(28):4158-4170, 2007.
Sakuragi et al., *Mech. Dev.* 13 (2): 114-23, 2006.
Schier et al., *Gene,* 169(2):147-155, 1996.
Serpe et al., *Dev. Cell,* 14:940-953, 2008.
Smadja et al., *Arterioscler. Thromb. Vase. Biol.,* 28(12):2137-2143, 2008.
Stemmer, *Nature* 370:389-391, 1994.
Suzuki et al., *Proc. Natl. Acad. Sci. USA,* 105(37):13781-13786, 2008.
Szoka and Papahadjopoulos, *Proc. Natl. Acad. Sci. USA,* 75:4194 4198, 1978.
Tomarev et al., *Mol. Neurobiol.,* 40(2): 122-38, 2009.
Umulis, *J. R. Soc. Interface:* 6(41):1179-91, 2009.
Valdimarsdottir et al., *Circulation,* 106(17):2263-2270, 2002.
Vandesompele et al., *Genome Biol.,* 3(7):34, 2002.
Vogt et al., *J. Cell Biochem.,* 98(5):1196-1202, 2006.
Walsh et al., *Trends Cell Biol.,* 20(5):244-256, 2010.
Winnier et al., *Genes Dev.,* 9(17):2105-2116, 1995.
Wong et al., *Gene,* 10:87-94, 1980.
Yancopoulos et al., *Nature,* 407:242-248, 2000.
Zeng et al., *FEBS Lett.,* 571:74-80, 2004.
Zhang et al., *J. Biol. Chem.,* 282:20002-20014, 2007.
Zheng et al., *Dev. Neurosci.,* 26(2-4):181-196, 2004.
Zhou et al., *Cardiovasc. Res.,* 76(3):390-399, 2007.

---

The invention claimed is:

1. A method of inhibiting angiogenesis in a subject having an angiogenic condition, comprising administering to the subject a composition comprising an antibody or a nucleic acid encoding the antibody, wherein the antibody recognizes and binds to (i) an epitope within amino acid positions 86-99 of SEQ ID NO:1 (human Olfml3 protein) or (ii) an epitope within amino acid positions 390-403 of SEQ ID NO:1, inhibits the binding of human Olfml3 protein to BMP4 protein and reduces the number of pericytes in vessels, wherein the antibody is a monoclonal antibody or an antigen-binding fragment thereof.

2. The method of claim 1, wherein the subject has a tumor.

3. The method of claim 2, wherein the antibody reduces the tumor size.

4. The method of claim 1, wherein the antibody fragment is Fab, Fab', Fab'-SH, F(ab')$_2$, or scFv.

5. The method of claim 1, wherein the antibody is attached to an agent to be delivered to an angiogenic cell.

6. The method of claim 5, wherein the agent is a cytotoxic agent, a cytokine, an anti-angiogenic agent, a chemotherapeutic agent, a diagnostic agent, an imaging agent, a radio-isotope, a pro-apoptosis agent, an enzyme, a hormone, a growth factor, a peptide, a protein, an antibiotic, an antibody or fragment thereof, an imaging agent, an antigen, a survival factor, an anti-apoptotic agent, a hormone antagonist, a virus, a bacteriophage, a bacterium, a liposome, a microparticle, a magnetic bead, a microdevice, a cell, a nucleic acid or an expression vector.

7. The method of claim 1, wherein the composition further comprises a lipid component.

8. The method of claim 7, wherein the lipid component forms a liposome.

9. The method of claim 7, wherein the lipid component is 1,2-dioleoyl-sn-glycero-3-phosphatidylcholine (DOPC), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, dilinoleoylphosphatidylcholine distearoylphophatidyletnanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), lysophosphatidylethanolamine, phosphatidylserine, phosphatidylglycerol, dimyristoyl phosphatidylserine ("DMPS"), dipalmitoyl phosphatidylserine ("DPPS"), brain phosphatidylserine ("BPS"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), dioleoylphosphatidylglycerol ("DOPG"), cholesterol or polyethyleneglycol (PEG).

10. The method of claim 1, wherein the subject is a human subject.

11. The method of claim 1, wherein the angiogenic condition is a cancer.

12. The method of claim 11, wherein the cancer is breast cancer, lung cancer, prostate cancer, ovarian cancer, brain cancer, liver cancer, cervical cancer, colorectal cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia.

13. The method of claim 1, wherein the angiogenic condition is an ocular neovascularization, an arterio-venous malformation, coronary restenosis, peripheral vessel restenosis, glomerulonephritis, rheumatoid arthritis, pancreatitis, a bowel disease, an ischemic cardiovascular pathology, or a chronic inflammatory disease.

14. The method of claim 1, wherein the antibody recognizes amino acid positions 86-99.

15. The method of claim 1, wherein the antibody recognizes amino acid positions 390-403.

* * * * *